United States Patent
Pratx et al.

(10) Patent No.: US 8,274,054 B2
(45) Date of Patent: Sep. 25, 2012

(54) METHOD AND APPARATUS FOR IMAGING USING ROBUST BAYESIAN SEQUENCE RECONSTRUCTION

(75) Inventors: Guillem Pratx, Stanford, CA (US); Craig S. Levin, Palo Alto, CA (US)

(73) Assignee: The Board of Trustees of the Leland Standford Junior University, Stanford, CA (US)

( * ) Notice: Subject to any disclaimer, the term of this patent is extended or adjusted under 35 U.S.C. 154(b) by 379 days.

(21) Appl. No.: 12/607,853

(22) Filed: Oct. 28, 2009

(65) Prior Publication Data
US 2010/0108894 A1   May 6, 2010

Related U.S. Application Data

(60) Provisional application No. 61/109,010, filed on Oct. 28, 2008.

(51) Int. Cl.
*G01T 1/00*   (2006.01)

(52) U.S. Cl. .................................. 250/363.02

(58) Field of Classification Search ............. 250/363.02
See application file for complete search history.

(56) References Cited

U.S. PATENT DOCUMENTS

| | | | |
|---|---|---|---|
| 7,732,773 B2 * | 6/2010 | Mihailescu et al. | ..... 250/363.04 |
| 8,063,380 B2 | 11/2011 | Levin et al. | |
| 2007/0253530 A1 * | 11/2007 | Mihailescu et al. | ........... 378/22 |

OTHER PUBLICATIONS

Boggs et al., "Event reconstruction in high resolution Compton telescopes", Astron. Astrophys. Suppl. Ser. 145, 311-321 (2000).
Chinn et al., "A Maximum NEC Criterion for Compton Collimation to Accurately Identify True Coincidences in PET", IEEE Transactions on Medical Imaging, vol. 30, No. 7, Jul. 2011.
Gu et al., "Effects of multiple-interaction photon events in a high-resolution PET system that uses 3-D positioning detectors", Med. Phys. 37 (10), Oct. 2010.
Oberlack et al., "Compton scattering sequence reconstruction algorithm for the liquid xenon gamma-ray imaging telescope (LXeGRIT)", arXiv:astop-ph/0012296v1, Dec. 13, 2000.
Pratx et al., "Bayesian reconstruction of photon interaction sequences for high-resolution PET detectors", Phys. Med Biol. 54 (2009) 5073-5094, Aug. 4, 2009.
Schmid et al., "A γ-ray tracking algorithm for the GRETA spectrometer", Nuclear Instruments and Methods in Physics Research A 430 (1999) 69-83.
Van der Marel et al., "Backtracking as a way to reconstruct Compton scattered γ-rays", Nuclear Instruments and Methods in Physics Research A 437 (1999) 538-551.

* cited by examiner

*Primary Examiner* — Constantine Hannaher
(74) *Attorney, Agent, or Firm* — Greer Burns & Crain Ltd

(57) ABSTRACT

Methods and systems for determining a sequence of energy interactions in a detector. A plurality of discrete energy interactions is received in a plurality of detector voxels. A plurality of possible sequences of interaction is formed based on the received plurality of discrete energy interactions. For each of the plurality of possible sequences of interaction, an a posteriori probability is computed, where the a posteriori probability is based on a likelihood that the possible sequence of interaction is consistent with the received plurality of discrete energy interactions. Additionally or alternatively, the a posteriori probability may be based on an a priori probability. One of the formed plurality of possible sequences of interaction is selected based on the computed a posteriori probability.

25 Claims, 13 Drawing Sheets

```
For each event:
  Form the set of all permutations with N elements
  For each permutation:
    Generate 16 384 realizations of the positions in the detector voxels
    For each realization
      Compute the hypothetical energy depositions
      Compute the hypothetical energy variance
      Compute the hypothetical scatter angles
      Evaluate the likelihood
      Compute the prior probability
      Evaluate the MAP objective
    Average the MAP objective
  Select the permutation with maximum objective value
  Position PMIE at the location of estimated earliest interaction
```

```
For each event:
    Form the set of all permutations with N elements
    For each permutation:
        Generate 16 384 realizations of the positions in the detector voxels
        For each realization
            Compute the hypothetical energy depositions
            Compute the hypothetical energy variance
            Compute the hypothetical scatter angles
            Evaluate the likelihood
            Compute the prior probability
            Evaluate the MAP objective
        Average the MAP objective
    Select the permutation with maximum objective value
    Position PMIE at the location of estimated earliest interaction
```

FIG. 5

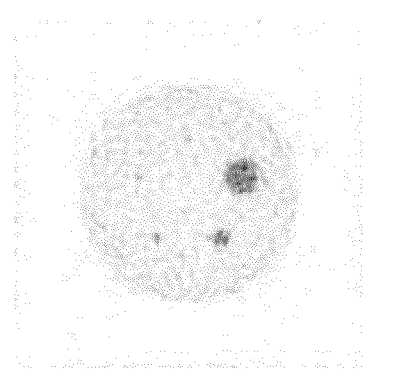
FIG. 10A
FIG. 10B
FIG. 10C
FIG. 10D

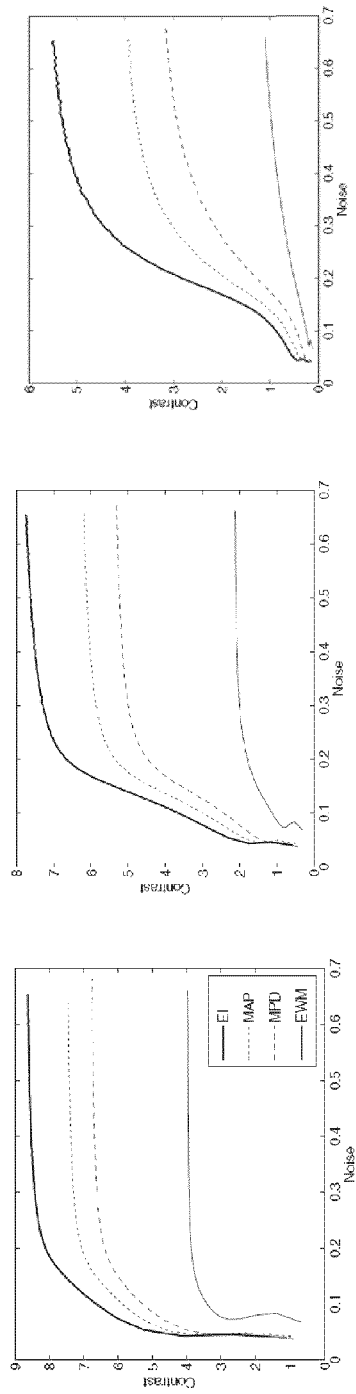
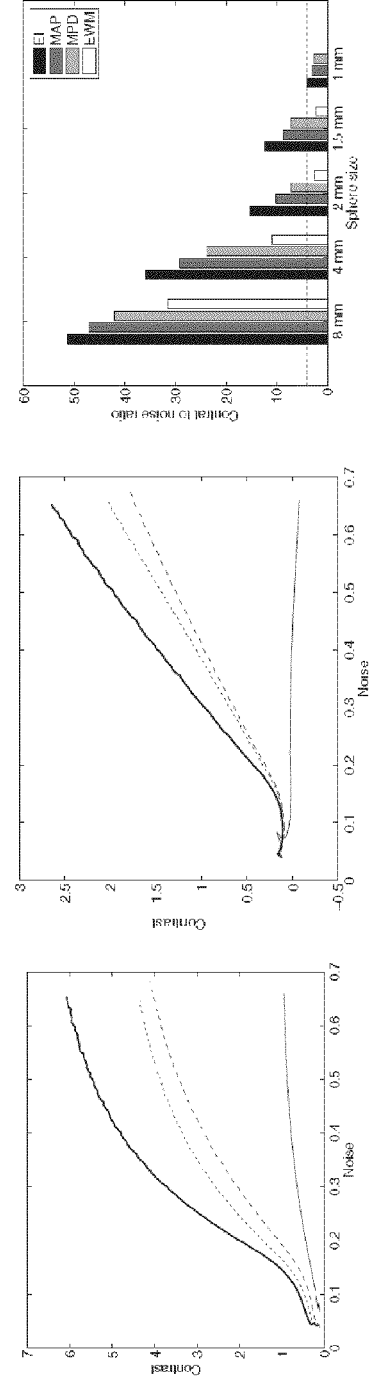
FIG. 11A
FIG. 11B
FIG. 11C
FIG. 11D
FIG. 11E
FIG. 11F

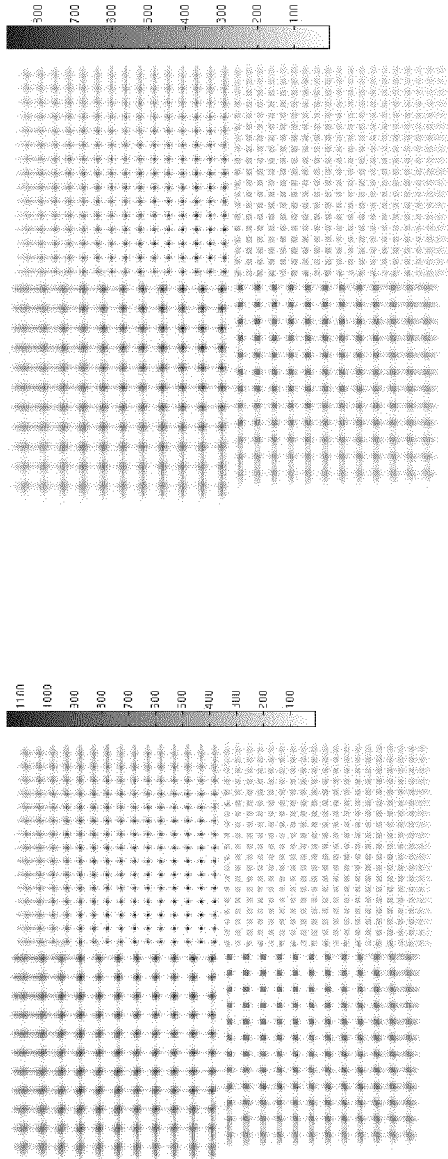
FIG. 12A
FIG. 12B
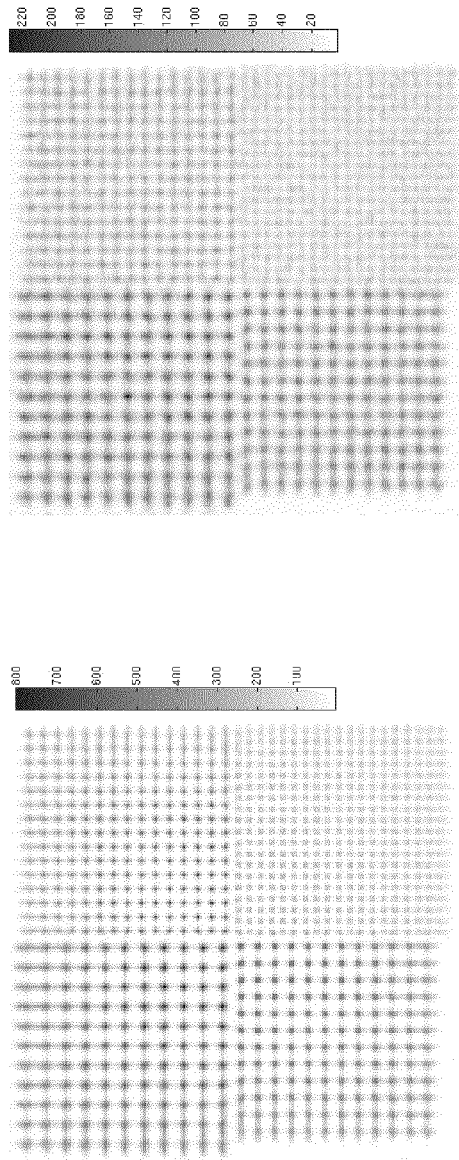
FIG. 12C
FIG. 12D

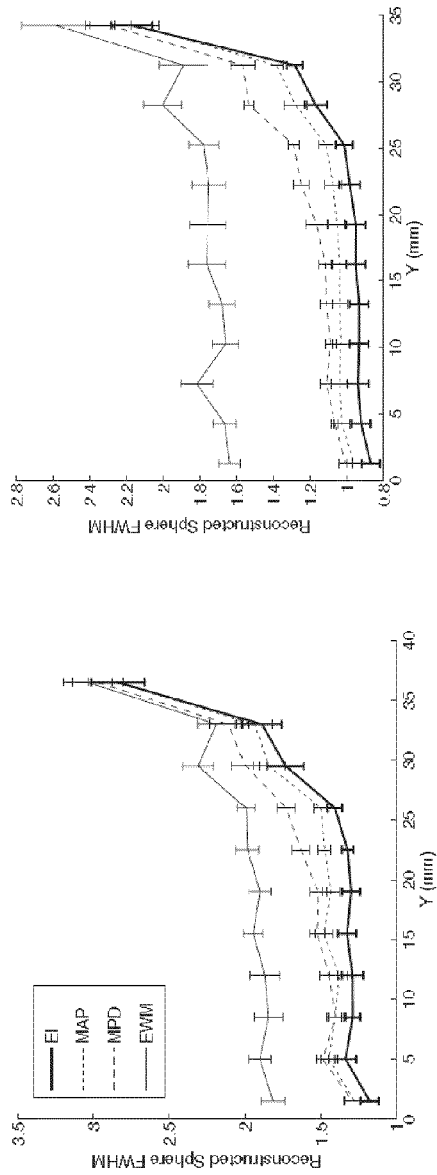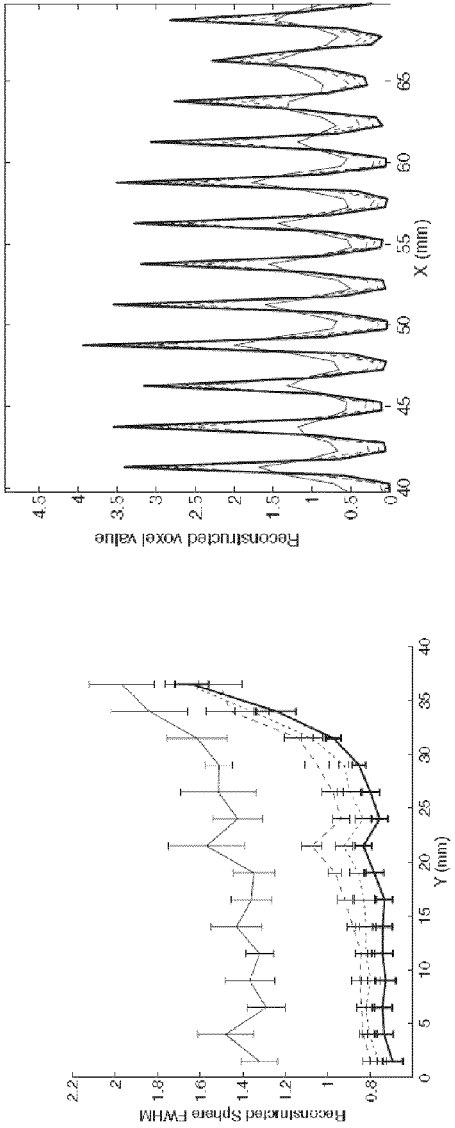
FIG. 13B
FIG. 13D
FIG. 13A
FIG. 13C

METHOD AND APPARATUS FOR IMAGING USING ROBUST BAYESIAN SEQUENCE RECONSTRUCTION

PRIORITY CLAIM AND REFERENCE TO RELATED APPLICATION

This application claims the benefit of U.S. Provisional Application Ser. No. 61/109,010, filed Oct. 28, 2008, under 35 U.S.C. §119, which is incorporated by reference herein.

STATEMENT OF GOVERNMENT INTEREST

This invention was made with government support under grants R01 CA119056, R33 EB003283 and R01 CA120474 awarded by National Institutes of Health (NIH). The government has certain rights in the invention.

FIELD OF THE INVENTION

Fields of the invention include methods, apparatus, and systems for imaging. Example applications of the invention include imaging using gamma ray detectors.

BACKGROUND OF THE INVENTION

Gamma ray detectors, based on scintillator, semiconductor, or gaseous materials, can be used to absorb, detect, and localize gamma rays. They are useful in a wide variety of applications ranging from medical imaging to astronomy and homeland security.

One nonlimiting example imaging application is positron emission tomography (PET). In PET and other applications, an event produces a gamma ray photon pair. Using detectors, a line of response (LOR) is determined for the photon pair, and multiple LORs are used to image a subject. Single events may also be used in certain imaging methods by determining an incoming direction. Detectors having good energy and spatial resolution provide a potential for high-resolution image detection systems.

However, in a significant number of events, one annihilation photon deposits all its energy across multiple detector elements. Such events, which are referred to herein as photon multiple interactions events (PMIEs), affect the reliability of current imaging methods. A nonlimiting example PMIE occurs when the photon undergoes inter-crystal scatter (ICS). For example, during a PMIE, depending on the gamma ray energy and the detector material (effective atomic number, density, and thickness), one gamma ray photon might produce a sequence of multiple discrete interactions in the detector, depositing its energy across multiple detector elements, due to Compton scatter and other physical effects. Due to the very short interaction time, it can be difficult to determine the actual interaction sequence.

For a high-resolution detector, a large percentage of the recorded single events and recorded coincidences include PMIEs. However, because it is desirable for an image reconstruction to include all recorded events for high sensitivity, ICS events should be positioned as accurately as possible. Because the earliest interaction defines the correct LOR or incoming direction for an event (subsequent interactions are not aligned with the true LOR or direction because Compton scatter deviates the annihilation photon from its linear trajectory, and an incorrect LOR causes loss of contrast, quantitative accuracy, and spatial resolution), it is useful to know the order of the interactions.

SUMMARY OF THE INVENTION

Methods and systems for determining a sequence of energy interactions in a detector are provided according to example embodiments of the present invention. In an example method, a plurality of discrete energy interactions is received in a plurality of detector voxels. A plurality of possible sequences of interaction is formed based on the received plurality of discrete energy interactions. For each of the plurality of possible sequences of interaction, an a posteriori probability is computed, where the a posteriori probability is based on a likelihood that the possible sequence of interaction is consistent with the received plurality of discrete energy interactions. Additionally or alternatively, the a posteriori probability may be based on an a priori probability. One of the formed plurality of possible sequences of interaction is selected based on the computed a posteriori probability.

BRIEF DESCRIPTION OF THE DRAWINGS

FIG. 5 shows an example maximum a posteriori (MAP) positioning algorithm according to embodiments of the present invention;

FIG. 6A shows three beams, with incident angles 0, 30, and 60 degrees, that were simulated; FIG. 6B shows a contrast phantom, including a 2.5 cm radius, 6 cm long cylinder filled with a warm solution of activity, in which were placed five hot spheres of size 1, 1.5, 2, 4, and 8 mm; and FIG. 6C shows a hot sphere phantom, including four sphere patterns, all in the same central plane;

FIG. 8 shows point-spread functions (PSFs) for four positioning methods, Earliest Interaction (EI), MAP, Minimum Pair Distance (MPD), and Energy Weighted Mean (EWM), where

FIG. 10 shows a contrast phantom, reconstructed with 100 iterations of list-mode 3D OSEM, where the phantom included a 2.5 cm radius water-filled cylinder, in which were placed five hot spheres of diameters 1, 1.5, 2, 4, and 8 mm, and where four positioning schemes were used: EI (FIG. 10A), MAP (FIG. 10B), MPD (FIG. 10C), and EWM (FIG. 10D);

FIGS. 11A-F show reconstructed hot spheres contrast as a function of noise, at different sub-iteration numbers for 8 mm (FIG. 11A), 4 mm (FIG. 11B), 2 mm (FIG. 11C), 1.5 mm (FIG. 11D), and 1 mm spheres (FIG. 11E); and where FIG. 11F shows peak contrast-to-noise ratio (CNR), computed between iteration number 10 and 100;

FIG. 12 shows the reconstructed images at 50 iterations for the four example positioning methods (EI, MAP, MPD, and EWM, respectively); and FIGS. 13A-13D show reconstructed sphere size for four positioning methods, measured by fitting a Gaussian mixture with offset to 1D profiles through the reconstructed volume, where FIG. 13A shows 1.75 mm spheres, FIG. 13B shows 1.5 mm spheres, FIG. 13C shows 1.25 mm spheres, and FIG. 13D shows a profile through the 1.75 mm spheres for the four positioning methods.

DETAILED DESCRIPTION

Figure 1:
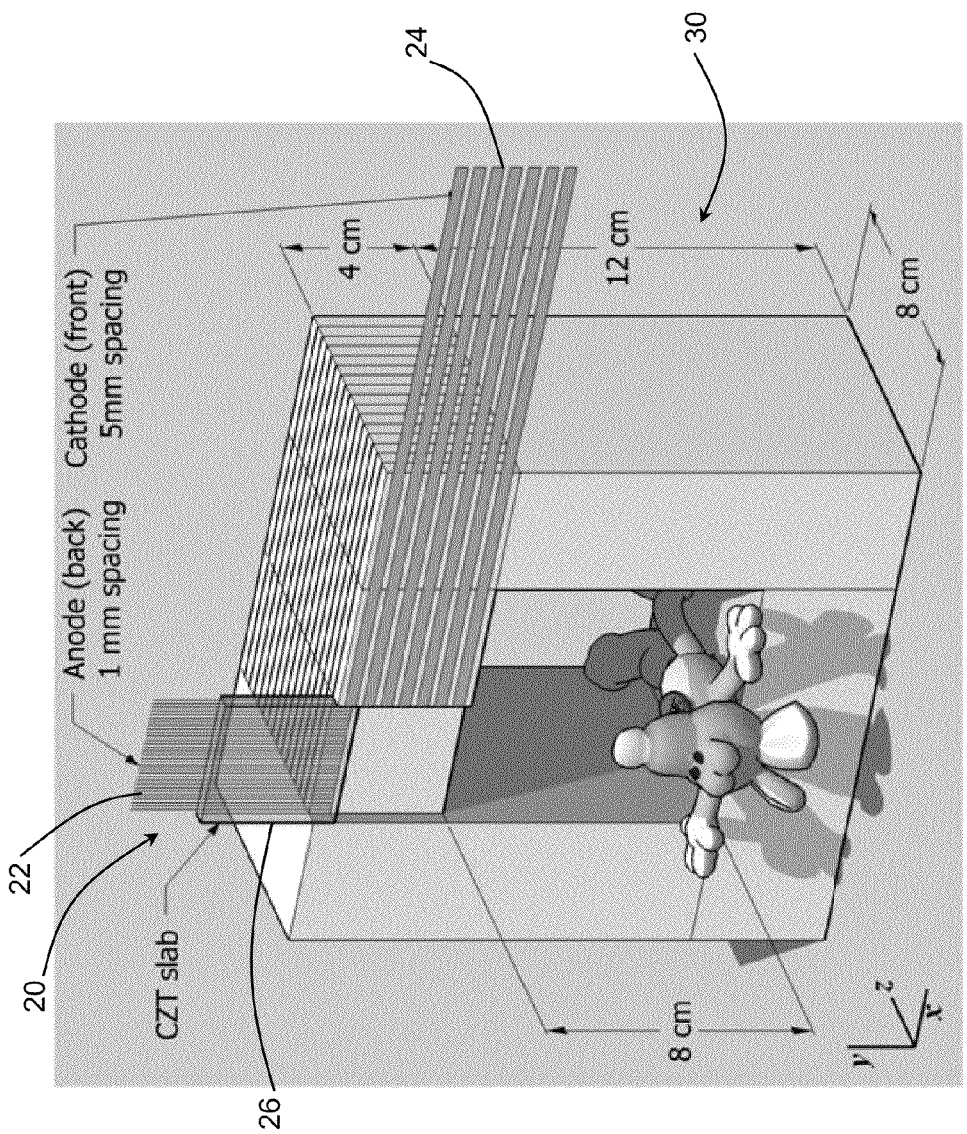
FIG. 1 shows an example CZT detector module for use with example embodiments of the present invention.

When multiple interactions are recorded, it is useful to know the order of the interactions. For example, the first interaction carries the most accurate position information for the incoming gamma ray. In addition, accurately sequencing the multiple interactions can be used to estimate the incoming direction of a gamma ray.

The ability to correctly position PMIEs greatly affects the global performance of imaging systems, such as but not limited to PET systems based on CZT detectors. Discarding such events is not a desirable solution because such events are part of a large fraction (e.g., 93.8%) of all the recorded coincidences. Conventional positioning schemes degrade both contrast and resolution, reduce the image's quantitative accuracy, and affect the detectability of hot lesions. Simple approaches help improve the image quality but are outperformed by more advanced positioning schemes that use more of the information available in an optimal way.

Bayesian methods according to embodiments of the present invention can combine prior information and measurements to identify the most probable sequence. Example robust Bayesian methods, based on maximum a posteriori (MAP), are disclosed for reconstructing the order of sequences of interactions that occur in detectors, thereby allowing one to identify the crystal of entry. An example sequence reconstruction problem is formulated using a robust (e.g., stochastic) statistical framework that takes into account the uncertainties in measuring the position and energy of every interaction. A particular example reconstructed sequence both maximizes the agreement with the data measurements and a priori probabilities based on the physics of gamma ray transport.

An embodiment of the invention is a method, apparatus, and/or system that determines (e.g., estimates) the correct sequence of a plurality of energy (e.g., gamma ray) interactions by using a robust statistical method, such as Bayesian estimation. Methods for determining a line of response (LOR) for incoming photons, for determining a direction of a single incoming photon, for selecting a first and/or subsequent interactions, for determining whether to consider or reject a particular event, and/or for imaging a subject by estimating the correct sequence of incoming photons are also provided under example embodiments of the present invention. Reconstructing a complete sequence of interactions for each photon can provide a reliable way to select an earliest interaction because it ensures that all the interactions are consistent with one another.

In an example method, for a plurality of energy (e.g., gamma ray) interactions, a plurality of possible sequences of interaction is formed based on received photon interactions in a plurality of detector voxels. For example, the received photon interactions may include received signals corresponding to a plurality of particular detector voxel locations and a plurality of energy measurements. As a result, as one nonlimiting example, if three detectors are hit during a PMIE, the received signals can be used to determine the particular detectors that are hit (x, y, z), and the energy measured ($E_m^{(1)}$, $E_m^{(2)}$, $E_m^{(3)}$). Unknown are the order of interactions $\sigma$, the energy deposited $E_D$, and the location $\omega$ of the interactions within the detector voxel (energy measurements have additive Gaussian noise, and detector pixel identification is noise-free).

The plurality of possible sequences preferably includes all possible permutations of the order of the interactions. Thus, in an example method, all of the possible sequences are formed. For each possible sequence, an a posteriori probability is computed.

Preferably, this probability is based in part on a maximum likelihood evaluation, e.g., an evaluation of the likelihood that a particular sequence of interactions is consistent with the observations (and in more particular examples, consistency of the energy measurements with the position measurements). For example, sequences including each of the possible permutations may be tested and compared to the observed energy information. As a nonlimiting example, for each sequence to be tested, one or more hypothetical energy calculations can be performed, and the result can be compared to the observed energy to evaluate a likelihood. In certain embodiments, for example, the hypothetical energy depositions can be computed using Compton kinematics.

Further, the a posteriori probability may be calculated based in part on prior knowledge, which is especially helpful when the measurements are noisy and/or unreliable. As a nonlimiting example, a prior distribution can be obtained by computing a total cross-section for each of the possible trajectories, based on the physics of gamma ray transport, to model the non-uniform probabilities for a sequence to be generated. Thus, before the energy measurements are made (though not necessarily), the relative a priori distribution can be inferred based on prior knowledge. Example types of prior knowledge and consideration criteria that may be used are provided in example embodiments of the present invention. However, methods of the present invention are not to be limited to using the particular types of prior knowledge described in examples herein. Individual or multiple criteria may be used.

In a particular example, if $\omega$, the uniform distribution inside the detector pixel is known, and $\sigma$ are discrete values (card.=N!) an example method solves maximize $L(\sigma,\omega) = P(E_m = E_d(\sigma,\omega)|(\sigma,\omega))$ where $E_d(\sigma,\omega)$ is computed using Compton kinematics, and $E_m$ is Gaussian distributed. If $\omega$ is unknown, an example method solves maximize $E_\omega L(\sigma,\omega)$
maximize $\min_\omega L(\sigma,\omega)$
maximize $L(\sigma, E\omega)$ The first two can be solved, in a nonlimiting example, using Monte-Carlo or other sampling on $\omega$ (e.g., using a GPU).

An example a posteriori probability objective combines the likelihood of the sequence, which measures the consistency of the energy measurements with the position measurements, and an a priori probability, which models the non-uniform probabilities for a sequence to be generated, and penalizes sequences that are unlikely based on photon attenuation and Compton scatter. Nonlimiting example methods for combining the a posteriori probability and the a priori probability include multiplying and adding the probabilities. As a nonlimiting example, the likelihood result may be multiplied by the a priori result to provide an objective value. In an example embodiment, a parameter may be used to control the respective influence (weight) of the likelihood and the prior model (e.g., the parameter may be used as a coefficient or exponent). The sequence having the maximum objective value is selected, and the location of the estimated earliest interaction is used to position the PMIE. In this way, example methods of the present invention consider both the detector measurements and the physics of gamma ray transport in determining the interaction sequence.

To improve the robustness of the Bayesian method, a distribution of multiple gamma ray tracks within the detector voxels can be generated in example embodiments of the present invention using stochastic methods. As a nonlimiting example, a random distribution of multiple gamma ray paths within a particular detector voxel can be generated by using Monte-Carlo sampling. The average objective over these multiple interaction paths can then be maximized. For example, for each permutation of the order of the interaction, possible realizations of the positions can be determined by, for each detector voxel in a group of multiple interactions, selecting at least one of a plurality of distributed positions within the detector voxel. This example method accounts for the finite spatial resolution of the detectors, as opposed to merely assuming that the center of a particular detector voxel is the correct interaction location. The random distributions can be used for a likelihood calculation, an a priori probability, or both. This method may require more computational resources than needed if only the center of the detector voxel is considered, but it provides significantly more robust results, as the determined path between multiple detector voxels can vary greatly depending on the particular path taken within each detector voxel. The number of realizations generated can be selected based on available computation time and/or resources, as nonlimiting examples. Distributed computing (e.g., parallel computing) may be used in some example embodiments to generate and/or evaluate particular realizations.

In an example robust method, the determined objectives for each realization are combined, for instance, averaged, to determine a maximum likelihood objective for that permutation. As a nonlimiting example, if a random distribution of gamma ray paths within a particular detector voxel is generated by using Monte-Carlo sampling, a likelihood may be computed using Monte-Carlo integration. Other methods for averaging the determined objectives, or other methods for combining the objectives, are contemplated as well (e.g., weighted average, multiplicative average, taking a worst case scenario, etc.) The average objective is thus maximized over these multiple distributed interaction paths based on the computed a posteriori probability. Accordingly, this example maximum likelihood criterion seeks the sequence of interactions that has the greatest statistical consistency with the observations by the detector, and accounts for any noisy and unreliable measurements.

Example methods according to the present invention provide a robust statistical framework for accurately estimating the sequence of gamma ray interactions with a high success rate. Factors such as the finite spatial resolution of the gamma ray detector, the noise distribution of the energy measurements, and/or the non-uniform a priori distribution of the sequences based on the physics of photon transport can be accounted for in example methods.

It is also contemplated that a sequence determination may be made based on only the maximum likelihood criterion (to assess consistency with observations), maximum a posteriori criteria based on prior knowledge, and/or generated distribution paths within individual detector voxels, or any combination of these three. While considering all three general criteria is preferred, the present invention is not to necessarily be limited to such consideration.

An example imaging system according to embodiments of the present invention includes a source of emitted photons (though other imaging systems may be separate from the source of emitted photons), and one or more detectors positioned to receive emitted photons and generate signals. The source of emitted photons may vary as will be appreciated by one of ordinary skill in the art, and the present invention is not to be limited to a particular source. A nonlimiting example source of emitted photons is a body into which a radioactive tracer has been introduced.

The one or more detectors should be able to detect individual interaction coordinates (e.g., individual detector voxels) and energies. A nonlimiting example for the one or more detectors is a cadmium-zinc-telluride (CZT) detector module, though others (e.g., lutetium oxyorthosilicate (LSO) coupled to thin position-sensitive avalanche photodiodes) are also applicable. An example detector module provides signals for 3-D positioning as well as energy. The pitch with which electrode strips are deposited determines the intrinsic spatial resolution. This example detector module also provides a pixilated design, which is employed by example embodiments of the present invention. However, the present invention is not to be limited to the imaging devices and systems specifically described herein, including those using a CZT detector module. Suitable power supplies, signal lines, etc. are coupled to the one or more detectors, as will be understood by those of ordinary skill in the art.

The one or more detectors are coupled by suitable electrical and/or optical couplers to a receiver and signal processor (which can include one or multiple receivers and one or multiple signal processors), which processes the signals produced by the one or more detectors. The receiver, such as but not limited to pulse processing electronics, may be any suitable receiver, and may be combined with or separate from the signal processor. A nonlimiting example signal processor is provided by a computing device, such as but not limited to a computer. A signal processor configured to perform methods of the present invention, e.g., a suitably configured computer, computer hardware, or computing device, is also contemplated to be part of the present invention. Further, embodiments of the present invention may also be provided by hardware devices, media of any appropriate type or design, a propagated signal, etc., that can be used to configure a signal processor to perform one or more example methods of the present invention (as a nonlimiting example, media containing executable instructions that when executed cause a computer to perform example methods of the present invention). The signal processor can be powered by any suitable power supply. A result may be displayed on a suitable display, stored in memory, storage (such as but not limited to disk storage), or any media, may be printed, and/or may be used for further processing. Accordingly, it is to be understood that when referring to methods herein, such description is also intended to refer to imaging devices, imaging systems, signal processors, computers, media, etc.

A robust (e.g., stochastic) Bayesian method according to example embodiments of the present invention can reconstruct more correct sequences than conventional methods. As a result, images reconstructed from datasets processed using example methods and systems of the present invention have higher SNR and show sharper features. An example method accounts for the pixilated nature of gamma ray detectors to provide improved performance.

Embodiments of the present invention may be used for several applications. As a nonlimiting example, in medical imaging, knowledge of the first interaction reduces the number of mispositioned photons, resulting in sharper images and higher SNR. For example, in medical imaging, it may be necessary to know the precise point-of-entrance of the gamma ray to accurately position the event. By forming the correct sequence, it is possible to determine the first interaction, which provides the most accurate position information. This feature is crucial to high-resolution gamma ray imaging systems in which multiple interactions are more likely to happen. Further, in medical imaging, knowledge of the first and second (or subsequent) interactions can be used to estimate the photon incoming direction and reject bad events (such as scatter and randoms) or incorporate events that are usually thrown away (e.g., singles). In gamma ray astronomy and homeland security applications, sequence reconstruction is critical to performing Compton imaging.

In addition, for a Compton camera, used in astronomy or homeland security, it is important to be able to accurately identify and sequence the first, the second, and, if available, sometimes the third interaction. This knowledge is useful to form the Compton cone and estimate both the point-of-entrance and the angle-of-entrance. This information can be used, as nonlimiting examples, to reconstruct sky images or image the presence of nuclear material in cargo trucks.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

Exploiting the full potential of high-resolution imaging methods can benefit from positioning events that deposit their energy, through Compton scatter, in multiple locations. Such high resolution imaging systems, such as but not limited to high-resolution positron emission tomography (PET) systems, use detector modules including small detection elements. As one nonlimiting example, semiconductor detectors made of Cadmium Zinc Telluride (CZT) directly sense the ionization signal created by the annihilation photon absorption. In these detectors, a strong electric field is established across the crystal by applying a relatively large potential difference on the two electrodes (anode and cathode) on either face of a monolithic crystal slab. When an incoming annihilation photon interacts with the atoms in the semiconductor crystal, electron-hole pairs are created and drift toward opposite faces, where they are detected by the device. The motion of the charge induces signals on the respective electrodes that are used to extract spatial, energy, and temporal information.

CZT detectors have good energy and spatial resolution. In addition, they can measure the 3-dimensional (3D) location (e.g., coordinates) of the energy deposition for building high-resolution individual interactions. As a result, they can provide high-resolution positron emission tomography (PET) systems with depth-of-interaction (DOI) measurement capability.

To exploit the full potential of CZT detector modules, however, the image reconstruction should be able to use the events in which annihilation photons deposit all their energy (e.g., 511 keV) across multiple detector elements or multiple locations, such as those that undergo inter-crystal scatter (ICS). For these events (referred to herein as PMIEs), the crystal of entrance is ambiguous. PMIEs are a major source of event positioning error in high-resolution PET systems, for example if the events are erroneously assumed to the wrong LOR, which in turn degrades spatial resolution, quantitative accuracy, and image contrast.

An example CZT detector module 20, as shown in FIG. 1, uses a set of parallel, thin rectangular strips 22 for the anode and an orthogonal set 24 for the cathode. For example, the cathodes 24 and the anodes 22 can be deposited on a front and a back face of a CZT slab 26, respectively. The x-y coordinate of the interaction (in the orientation shown in FIG. 1) is determined by the intersection of the strips 22, 24 on either side of the crystal slab 26 that record a signal above threshold. The pitch with which the electrodes are deposited determines the intrinsic spatial resolution. The z coordinates along the direction orthogonal to the electrode plane are determined using the ratio of the cathode to anode signal pulse heights. In an example imaging system, in this direction, the intrinsic resolution is below 1 mm full-width half-maximum (FWHM). In this example cross-strip electrode design, the signals can be multiplexed, thereby reducing the number of electronic channels required.

In a nonlimiting example small animal PET system 30, 40×40×5 $mm^3$ slabs 26 of CZT are arranged edge-on with respect to the incoming photons. The 8×8×8 $cm^3$ field-of-view (FOV) extends to the edge of the detectors, due to the detector's ability to read out the 3D coordinates of individual photon interactions. The intrinsic resolution in the x-y plane, determined by the electrode pitch, is 5 mm for the example cathode and 1 mm for the example anode. The axial and tangential intrinsic resolution for the system is therefore 1 mm. To mitigate the impact of parallax blurring, the depth coordinate is quantized to intervals of 5 mm. The detector voxel elements in this example system are 1×5×1 $mm^3$ in the coordinate system of FIG. 1.

CZT is a low Z material, and as a result its photo-fraction is low compared to other crystals. To preserve high photon detection efficiency, the geometry of the particular example system 30 is designed such that 511 keV photons see a minimum of 4 cm thick material. Still, in the CZT material for this example system 30, a large fraction (75.1%) of all events undergoes at least one Compton scatter. Because the detection voxels are small, the scattered photons usually escape into adjacent crystals. On average, a 511 keV photon deposits its energy in 2.2 detector voxels. Accordingly, in 93.8% of all the recorded coincident pairs in an example run, at least one annihilation photon underwent ICS. It is highly desirable to use all the events, including those for which the position is ambiguous, to preserve the system's high photon sensitivity (e.g., 17% at 800 μCi at the center, a 16-fold increase compared to using only events that deposit all their energy in a single detector voxel). However, the ability to correctly position these events strongly determines the quality of the images obtained from the example PET system 30.

A standard position sensitive PET detector uses light multiplexing in the scintillation crystal array and/or charge multiplexing in a position sensitive photodetector or associated readout circuit resulting in a few (typically four) readout channels. Such detectors estimate the photon interaction coordinates for each event by determining the weighted mean of the readout signals. Thus, individual interaction coordinates and their energies deposited cannot be determined in the standard PET detector. Fortunately, PMIEs are less frequent for standard large crystal elements, which are more likely to completely absorb the energy from multiple interactions.

In the example system 30 shown in FIG. 1, since the cross-strip electrode design is capable of recording the 3D coordinates and energy deposition for every interaction, it is possible to distinguish the photons that deposit their energy in a single detector voxel from those which deposit their energy in multiple detector voxels. The knowledge of every interaction position and energy can be used to infer the correct crystal of entrance and mitigate the effect of ICS positioning errors. The earliest interaction carries the most accurate position information because it best defines the correct line of response (LOR) along which the two annihilation photons traveled. In general, the time of each interaction is not known with sufficient accuracy to infer which interaction happened first, thus the order of the sequence of interaction must be reconstructed from the position and energy of individual interactions. Secondary interactions are useful for measuring the total energy of the event, or estimating the direction of the incoming photon.

Other PET systems, such as but not limited to systems where the crystal is individually coupled to the light detector, allow readout of multiple interactions from PMIEs. Examples include, but are not limited to, systems disclosed in Bergeron et al, Performance evaluation of the LabPET APD-based digital PET scanner, IEEE Nuclear Science Symp. Conf. Record, vol. 6, 2007, pp 4185-91; Spanoudaki, Development and performance studies of a small animal positron emission tomography with individual crystal readout and depth or interaction information, Dissertation Technische Universitt Munchen, 2008; Braem et al, Feasibility of a novel design of high resolution parallax-free Compton enhanced PET scanner dedicated to brain research, Phys. Med. Biol. 49, 2004, pp. 2547-62; Zhang et al., Performance characterization of a novel thin position-sensitive avalanche photodiode for 1 mm resolution positron emission tomography, IEEE Trans. Nucl. Sci. 54, 2007, pp. 415-21; and Levin et al., New imaging technologies to enhance the molecular sensitivity of positron emission tomography, Proc. IEEE 96, 2008, pp. 439-67, the contents of which are incorporated herein by reference.

These systems are example systems that can distinguish the photons that deposit their energy in a single detector voxel from those which deposit their energy in multiple detector voxels. This presents an opportunity to position PMIEs. Positioning methods can usually be classified in three categories: interaction selection, unconstrained positioning, and full sequence reconstruction.

In interaction selection, an estimate of the earliest interaction (EI) is selected from the finite set of all detected interactions, and used to position the PMIE. This class of methods exploits some form of correlation between the order of the interactions and properties of their energy and position. Example techniques include choosing the interaction with largest/second largest signal, the smallest depth of interaction, or the minimum distance to the other coincident photon. For sequences of more than two interactions, the order of subsequent interactions is not recovered.

In unconstrained positioning, the positioning problem is relaxed by allowing the positioning of PMIEs to be assigned to any location within the detection volume. For example, the energy-weighted mean scheme (EWM), used in conventional PET systems, combines the interaction locations linearly using the energy as weight.

Full sequence reconstruction is performed by assigning possible sequences (for example, every possible sequence) an objective value. For example, an objective can be chosen to favor sequences that are consistent with both the detector's measurements and/or the physics of γ-ray transport.

A number of objectives have been considered to penalize sequences that violate the kinematics of Compton scatter. These techniques are based on testing the consistency of redundant information. For example, the cosine of the scatter angle can be computed using the Compton formula, provided that the order of the sequence of interactions and the annihilation photon energy are known. This quantity can also be obtained directly from the interaction locations. The sum of the square of the differences of the scatter angle cosines can be used as an objective to assess that the sequence kinematics are valid. This scheme can be refined by weighting the summands by the measurement error. Another method forms the weighted sum of the absolute difference between the scatter angle computed from trigonometry and from Compton kinematics.

The objective can also be based on physical considerations, such as the probability that the annihilation photon follows a trajectory. The Klein-Nishina differential cross-section is one component of the trajectory probability. Other components can contribute to the trajectory probability, such as photoelectric cross section and exponential attenuation.

Another technique, backtracking, reconstructs the sequence backwards. Instead of performing a full search over the combinatorial space of all the sequences, this technique recovers the complete sequence of interactions sequentially by first identifying the photoelectric interaction, whose energy is assumed to be independent of the track properties, and then by retracing the interaction track backwards.

To reduce mispositioning errors, a robust Bayesian estimation method is provided according to embodiments of the present invention based on a maximum-a-posteriori (MAP) objective. An example method reconstructs the order of the sequence of interactions created by photons (e.g., 511 keV photons) in detectors such as the CZT detectors. The position of the event then can be assigned to the location of the estimated earliest interaction. The sequence reconstruction problem preferably is formulated using a robust statistical (e.g., stochastic) framework that takes into account the uncertainties in measuring the position and energy of each interaction. The reconstructed sequence both maximizes the agreement with the data measurements, and the a priori probability of the trajectory, based on the physics of gamma ray transport.

Example embodiments include a sequence reconstruction method that optimizes agreement with the measurements while also accounting for the trajectory total cross-section. Bayesian estimation provides an example framework to combine these two goals. Agreement with the measurements can be dealt with in an example embodiment using a maximum-likelihood (ML) approach, and the total trajectory cross-section can be described by a prior probability distribution. The combination (e.g., product) of the likelihood with the prior distribution yields the maximum a posteriori (MAP) objective. Using an example statistical framework has the advantage that measurement noise properties can be rigorously characterized in the objective. In addition, the example ML estimate is asymptotically efficient and unbiased.

A concern with some sequence reconstruction methods is that the exact location of each interaction within the detector voxel is uncertain. It is often assumed that the interactions occur at the center of the detector voxels, and this induces errors in the calculation of the objective. To mitigate this problem, a stochastic Bayesian estimation approach is used in example embodiments to provide a more robust method. In a particular example method, for all possible sequence orderings, the objective is averaged over many possible interaction paths, where the interaction location is sampled from 3D uniform distributions over the corresponding detector voxels. In a nonlimiting example embodiment, the possible interaction paths are produced by Monte-Carlo.

The MAP objective combines the likelihood objective and a prior probability distribution. A particular example method based on MAP will now be described with respect to the PMIE event shown in FIG. 2.

Stochastic Maximum-Likelihood

The maximum likelihood (ML) criterion is used to determine (e.g., seek) the sequence of interactions that has the greatest consistency (e.g., statistical consistency) with the observations. For an event comprising N interactions, N! hypotheses are tested in an example method. Each hypothesis describes a possible sequence of N interactions. The particular example ML procedure evaluates the likelihood of all the hypotheses and selects the one with the greatest likelihood.

Due to the pixilated nature of the detector (in this example, CZT detectors), the interaction position is quantized to the nearest detector voxel. The exact position $r_i$ of each interaction can be expressed as the sum of the center $d_i$ of the detector voxel (e.g., the nearest intersection of the electrodes) and the position quantization error $q_i$ $$r_i = d_i + q_i \qquad (1)$$

Figure 2A:
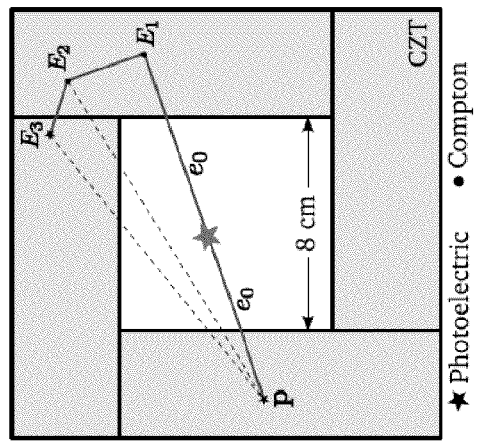
FIG. 2A shows an example coincident event recorded by an example PET system based on CZT cross-strip electrodes modules.

For example, in FIG. 2A, the solid line represents the annihilation photon trajectory. FIG. 2A shows an example coincident event recorded by an example PET system based on CZT cross-strip electrodes modules, including a pure photoelectric event (p, left) and a PMIE (right) with three interactions $E_1$, $E_2$, $E_3$. The incoming energy $e_0$ is 511 keV. In this specific example, there are six possible sequences, only one of which is correct (sequence 1, 2, 3). Incorrect sequences can result in mispositioning of the ICS event and misidentification of the LOR (dotted line).

Figure 2B:
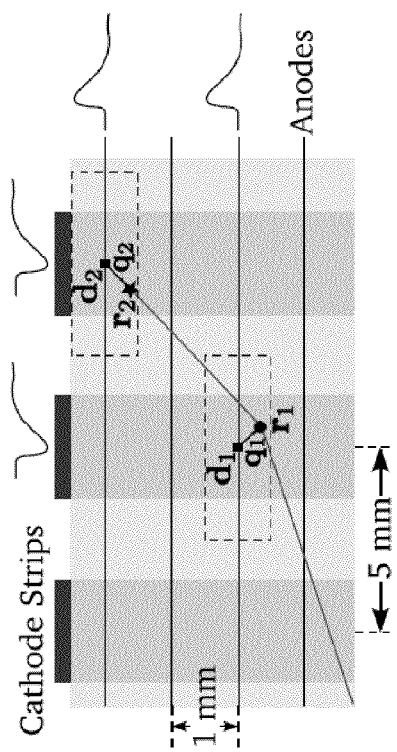
FIG. 2B shows how positions are noted for an example sequence of two interactions in the cross-strip CZT module.

FIG. 2B depicts how positions are noted for an example sequence of two interactions in the cross-strip CZT module. In FIG. 2B, the true interaction position $r_i$ of the energy deposition is quantized to the nearest intersection of the electrodes $d_i$. The quantization error is $q_i = r_i - d_i$. Electric signals are read out from the anodes and cathodes involved. Detector voxels are represented by dotted rectangles. The unknown position $q_i$ is assumed to be uniformly distributed within the detector voxel.

The permutations of $\{1, \ldots, N\}$ form a finite set $\mathcal{P}_{I\!N}$, of cardinality N!. Here, $\sigma = (\sigma_1, \ldots, \sigma_N)$ refers to an element of $\mathcal{P}_{I\!N}$. For example, (3, 1, 2) is an element of $\mathcal{P}_{I3}$. The set of all the possible sequences of N interactions can be mathematically represented by $\mathcal{P}_{I\!N}$.

The recorded energy deposition locations are numbered $j = 1, \ldots, N$. These indices are arbitrary and do not represent the true order of the interactions. The measurement $E_j$ of the energy deposited at the $j^{th}$ location $r_j$ in the detector (FIG. 2A) in an example method is subject to zero-mean Gaussian noise $n_j$, with variance $\Sigma_j^2$.

$$E_j = \epsilon_i + n_j, \; n_j \sim N(0, \Sigma_j), j = \sigma_i \qquad (2)$$

where $\epsilon_i$ denotes the true energy deposition for the $i^{th}$ interaction. The true energy depositions are indexed by i, the true interaction number, which is related to j by an unknown permutation $\sigma$.

Note that in formulating an ML objective, it is possible to compute analytically the energy deposited during a Compton scatter interaction. For example, given any permutation $\sigma$ in the order of the interactions, $\hat{e}_i(\sigma)$ is the hypothetical value of the photon energy between the ith and the (i+1)th interaction, computed from Compton kinematics. The hypothetical energy deposited by the ith interaction is denoted $\hat{\epsilon}_i(\sigma)$. Conservation of energy implies $$\hat{e}_i(\sigma) = \hat{e}_{i+1}(\sigma) + \hat{\epsilon}_i(\sigma) \qquad (3)$$

The first hypothetical energy deposition can be computed using $$\hat{\epsilon}_1(\sigma) = e_0 - \frac{e_0}{1 + \frac{e_0}{m_e c^2}(1 - \cos\hat{\theta}_1)}, \qquad (4)$$

$$\cos\hat{\theta}_1 = \frac{\langle r_{\sigma_1} - p \mid r_{\sigma_2} - r_{\sigma_1} \rangle}{\|r_{\sigma_1} - p\| \cdot \|r_{\sigma_2} - r_{\sigma_1}\|}$$

where $m_e$ denotes the mass of the electron and c the speed of light in vacuum. In this expression, it is assumed that the energy $e_0$ of the incoming photon and the position p of the other coincident photon pair are known. For PET, for instance, the incoming energy $e_0$ is set to 511 keV. When the other coincident pair also involves multiple interactions, p is estimated roughly, for example, by computing the center of mass.

In a similar fashion, for $i \leq N-1$, $\hat{\epsilon}_i(\sigma)$ can be evaluated recursively for any permutation $\sigma$:

$$\hat{\epsilon}_i(\sigma) = \hat{e}_{i-1} - \frac{\hat{e}_{i-1}}{1 + \frac{\hat{e}_{i-1}}{m_e c^2}(1 - \cos\hat{\theta}_i)}, \qquad (5)$$

$$\cos\hat{\theta}_i = \frac{\langle r_{\sigma_i} - r_{\sigma_{i-1}} \mid r_{\sigma_{i+1}} - r_{\sigma_i} \rangle}{\|r_{\sigma_i} - r_{\sigma_{i-1}}\| \cdot \|r_{\sigma_{i+1}} - r_{\sigma_i}\|}$$

For i=N, the energy of the annihilation photon is fully deposited through photoelectric interaction. Therefore, the last energy deposition is $$\hat{\epsilon}_N(\sigma) = \hat{e}_{N-1}(\sigma) \qquad (6)$$

The correct sequence $\sigma^{sol}$ satisfies $\hat{\epsilon}_i(\sigma^{sol}) = \epsilon_i$ for all i. However, only a noisy measurement $E_i$ of $\epsilon_i$ is known, and therefore the sequence which maximizes the likelihood that $\hat{\epsilon}_i(\sigma^{sol}) = E_{\sigma_i}^{sol}$ is chosen. Assuming the positions $q_i$ are known, the likelihood $L_q$ can be expressed as $$L_q(\sigma) = P(E_{\sigma_1} = \hat{\epsilon}_1(\sigma), \ldots, E_{\sigma_N} = \hat{\epsilon}_N(\sigma) \mid \sigma) \qquad (7)$$

$$= \prod_{i=1}^{N} \frac{1}{\sqrt{2\pi}\Sigma_i} \exp\left(-(E_{\sigma_i} - \hat{\epsilon}_i(\sigma))^2 / 2\hat{\Sigma}_i^2\right) \qquad (8)$$

because $n_i$ is a Gaussian-distributed random variable with variance $\Sigma_i^2$. The Hypothetical energy depositions $\hat{\epsilon}_i(\sigma)$ can be computed using equations (4), (5) and (6). The variance $\Sigma_i^2$ is a function of the energy deposition $\epsilon_i$. A model of the energy resolution for the detector is used, and a hypothetical variance $\hat{\Sigma}_i^2$ is computed using the hypothetical energy deposition $\hat{\epsilon}_i(\sigma)$. In the evaluation of an example method, $\hat{\Sigma}_i^2 = 1/2.35^2 \times ((6 \text{ keV})^2 + (2.2\% \times \hat{\epsilon}_i(\sigma))^2)$ was used, where 6 keV represents the noise floor of the electronics.

Figure 3:
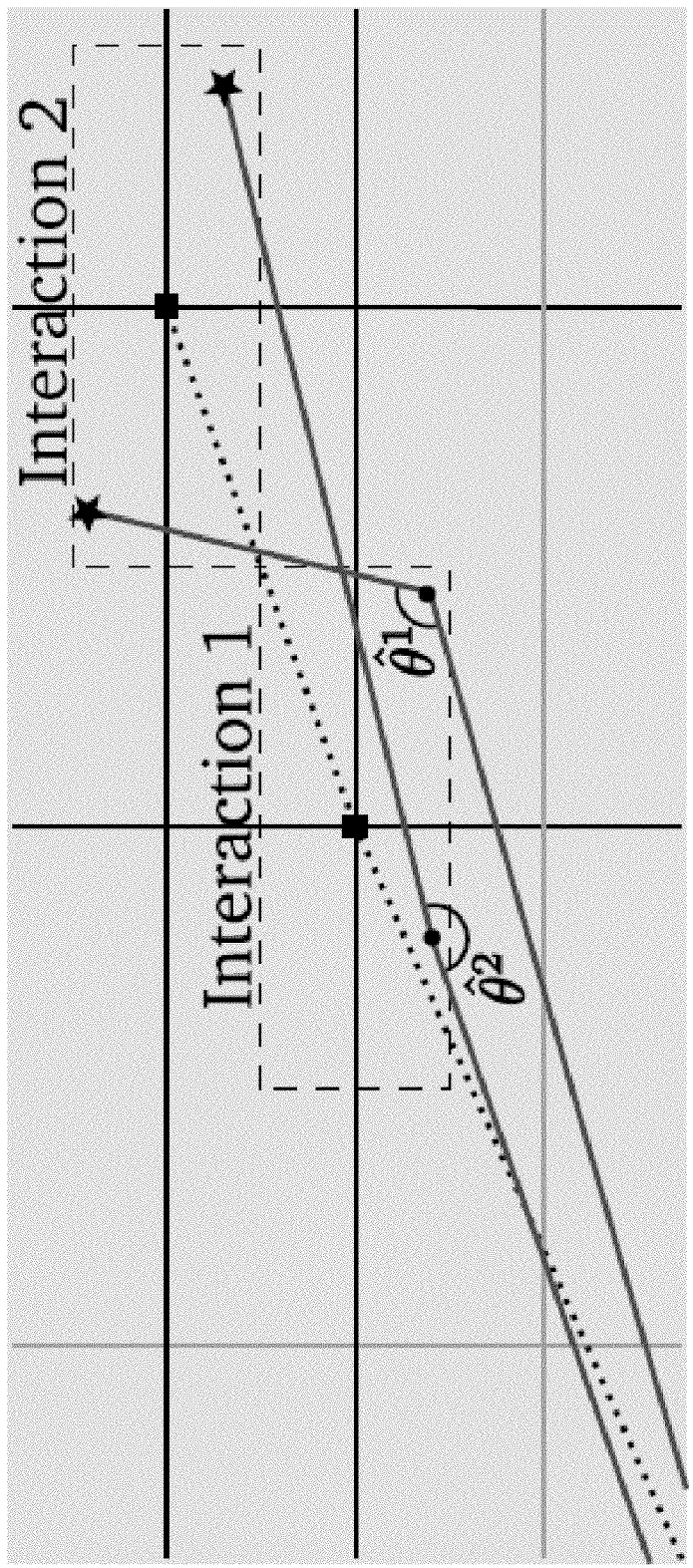
FIG. 3 shows energy depositions recorded in two locations.

In example operation, the optimization parameters $q_i$ are unknown. In order to compute the objective, they can be substituted by their expected value $E(q_i)$. For a uniform distribution, $E(q_i) = 0$, therefore the interaction locations are assumed to be at the detector voxel center $d_i$. However, the uncertainty on $q_i$ can result in important variations in the scatter angle $\theta_i$, which in turn cause significant errors in the objective, as shown in FIG. 3. In FIG. 3, energy depositions were recorded in two locations. One or more interactions have occurred in each of the detector voxels, delineated by dashed rectangles. The sub-voxel positions $q_1$ and $q_2$ of each interaction are unknown. If $q_1$ and $q_2$ are assumed to be zero, one obtains the trajectory represented by a dotted line. If a robust method is used instead, $q_1$ and $q_2$ are generated randomly and the objective is computed by averaging many trajectories, represented by solid lines. The scatter angle can vary substantially depending on the position of the interaction within each detector voxel.

An example robust method includes maximizing the likelihood expected value over q $$\max L(\sigma) = E_q L_q(\sigma) \quad (9)$$

This objective accounts for limited resolution of the detector and provides a robust estimator for the optimal sequence. The computation of L ($\sigma$) in an example method is performed by Monte-Carlo integration absent an analytical expression. Multiple realizations of the positions $q_i$, assumed to be uniformly distributed within the detector voxel, are generated. The objective is evaluated for each realization, and the average objective is then computed.

In an example performance of a method, a GeForce 9800 GX2 (NVIDIA) graphics processing unit (GPU) and the CUDA library (Nickolls et al., Scalable parallel programming with CUDA, ACM Queue 6, 2008, pp. 40-53) were used to accelerate the calculation of the expected value by Monte Carlo integration. Processing each PMIE involved computing the likelihood objective over 16,384 realizations. A Mersenne-twister random number generator was executed on a GPU to randomly sub-sample the detector voxels using a uniform distribution. The computation was decomposed into 32 blocks of 128 threads, resulting in a total of 4096 threads, each processing four realizations. The number of realizations was chosen to maximize performance, and can be reduced for faster processing. The 16,384 objective values were subsequently averaged on the CPU.

Maximum A Posteriori

The quality of the estimation can be enhanced by incorporating prior knowledge into the objective. This particularly helps when the measurements are noisy and unreliable. For estimating the order of the interactions in a PMIE, a prior probability distribution is obtained in example embodiments by computing the total cross-section for all N! trajectories. This cross-section is based on the physics of γ-ray transport. For example, before the energy measurements are made, the relative a priori distribution of the sequence of interactions can be inferred based on the Klein-Nishina differential cross-section and the photoelectric cross-section.

An example prior probability distribution $P_{prior}(\sigma)$ comprises three components: the probability $P_{prop}(\sigma)$ that the annihilation photon travels the distance linking two successive interactions without being attenuated; the probability $P_{comp}(\sigma)$ that the photon Compton scatters N-1 times, with angle $\theta_i$, each interaction being localized within a small control volume $\delta V_i$ centered on $r_i$; and the probability $P_{phot}(\sigma)$ that the photon is absorbed by the photoelectric effect within a small control volume $\delta V_N$ centered on $r_N$.

The first component $P_{prop}(\sigma)$ can be expressed as $$P_{prop}(\sigma) = \prod_{i=1}^{N-1} \exp(-\mu_{tot}(\hat{e}_i) \times \|r_{\sigma_{i+1}} - r_{\sigma_i}\|) \quad (10)$$

where $\mu_{tot}$ is the linear photon attenuation coefficient in the detector material (e.g., for CZT, an example coefficient from Berger et al., XCOM: photon cross sections database, NIST Standard Reference Database, 8 (XGAM), 1998), and $e_i$, the energy of the photon after interaction i, is computed from the Compton kinematics using equations (4) and (5).

The second component $P_{comp}(\sigma)$ can be obtained from the Compton scatter cross-section:

$$P_{comp}(\sigma) = \prod_{i=1}^{N-1} \frac{\mu_c(\hat{e}_i)}{\mu_{kn}(\hat{e}_i)} \int_{\phi=0}^{2\pi} \frac{d\sigma_{kn}}{d\theta_i} \quad (11)$$

where $$\int_{\phi=0}^{2\pi} \frac{d\sigma_{kn}}{d\theta_i} = \int_{\phi=0}^{2\pi} \frac{d\sigma_{kn}}{d\Omega_i} \frac{d\Omega_i}{d\theta_i} \quad (12)$$

$$= \int_{\phi=0}^{2\pi} \frac{d\sigma_{kn}}{d\Omega_i} \sin\theta_i d\phi \quad (13)$$

$$= 2\pi \sin\theta_i \frac{d\sigma_{kn}}{d\Omega_i} \quad (14)$$

is the differential Compton cross-section per unit of angle, which can be compared using the Klein-Nishina formula:

$$\frac{d\sigma_{kn}}{d\Omega_i} \propto \left(\frac{e_{i+1}}{e_i} - \left(\frac{e_{i+1}}{e_i}\right)^2 \sin^2\theta_i + \left(\frac{\hat{e}_{i+1}}{\hat{e}_i}\right)^3\right). \quad (15)$$

The Compton linear attenuation coefficient $\mu_{kn}(e_i)$ is computed by integrating the Klein-Nishina scatter cross-section over all angles:

$$\mu_{kn}(\hat{e}_i) = \int_{\phi=0}^{2\pi} \int_{\theta=0}^{\pi} d\sigma_{kn}. \quad (16)$$

Figure 4:
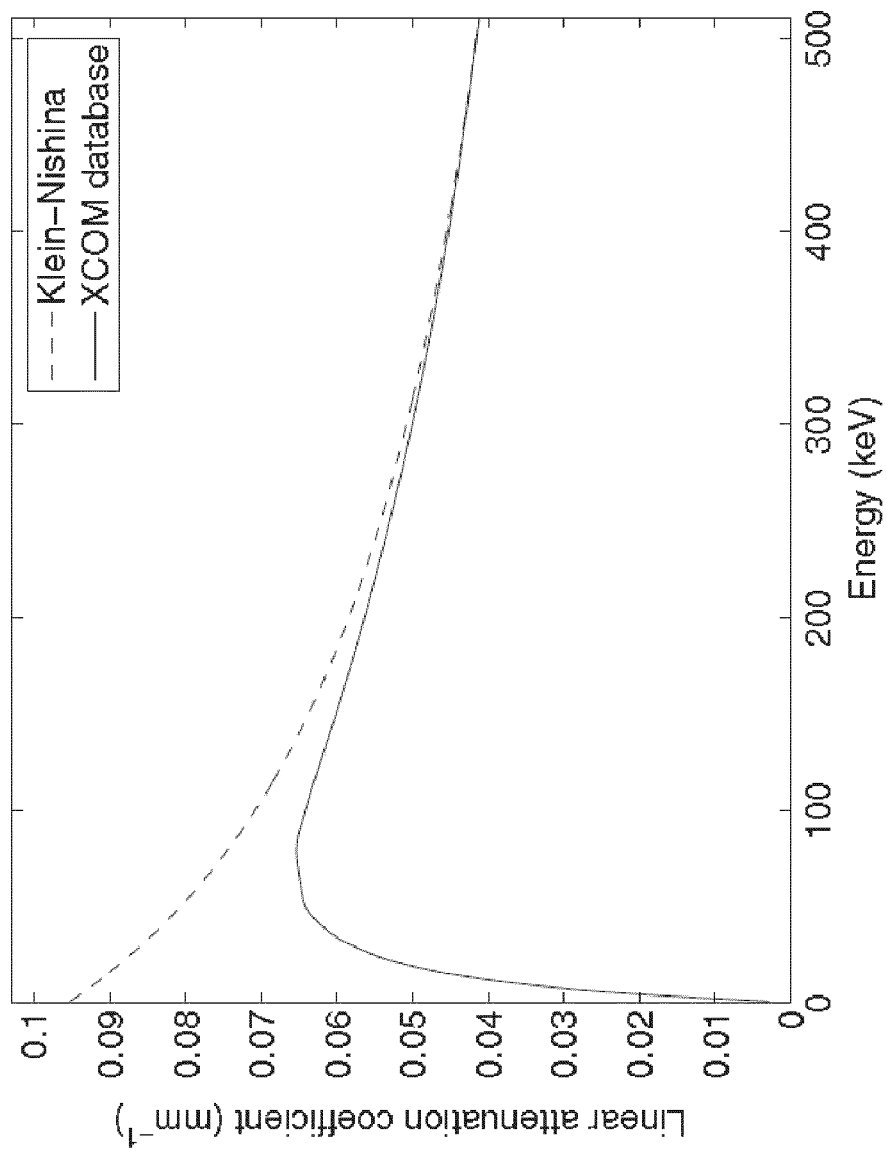
FIG. 4 shows a linear Compton scatter attenuation coefficient as a function of photon energy for CZT.

However, because the example model assumes the electron is free and at rest, $\mu_{kn}(e_i)$ is not accurate for low ($\leq 100$ keV) photon energy, as shown in FIG. 4. FIG. 4 shows linear Compton scatter attenuation coefficient as a function of photon energy for CZT. For this reason, equation (11) can be rescaled using the Compton scatter attenuation coefficient $\mu_c(e_i)$ obtained from published databases (e.g., Berger et al., XCOM: photon cross sections database, NIST Standard Reference Database, 8 (XGAM), 1998).

Please amend the paragraph beginning at line 10, page 24 as follows:

The resulting example prior distribution is the product of the three components $$P_{prior}(\sigma) = P_{prop}(\sigma) \times P_{comp}(\sigma) \times P_{phot}(\sigma). \quad (18)$$

Please amend the paragraph beginning at line 13 on page 24 as follows:

The example MAP objective is then formed by multiplying the example likelihood objective with the example a priori probability distribution $$P_{MAP}(\sigma) = L_q(\sigma)^{(1-\beta)} \times P_{prior}(\sigma)^\beta, \quad (19)$$

where β is a parameter weighing the prior probability and the likelihood. The ML estimate is obtained when β is zero. Note also that the objectives may be combined in other ways, for example by addition, with β and (1−β) as coefficients.

A simplified schematic of the complete example positioning algorithm is provided in FIG. 5.

Simulation of an Example CZT PET System

A fast Monte-Carlo package, GRAY (Olcott et al., GRAY: high energy photon ray tracer for PET applications, IEEE Nuclear Science Symp. Conf. Record, 2006, pp. 2011-5) was used to simulate an example PET system based on CZT cross-strip electrodes modules. The photoelectric effect and Compton scattering are the only physical processes included in GRAY. GRAY uses published databases (e.g., Berger et al., XCOM: photon cross sections database, NIST Standard Reference Database, 8 (XGAM), 1998) for computing the interaction cross-sections. The Compton scatter angular distribution is generated according to the Klein-Nishina formula. Individual interactions (hits) in the CZT detector module can be stored in list-mode. The list-mode dataset contains the accurate time, energy, and position of individual interactions.

After the simulation, the position of each event was processed to account for the limited spatial resolution of the system. Within one module, the spatial coordinates were binned to a grid of 1×5×1 mm³ detector voxels. When two interactions occurred in the same detector voxel (which was rare), they were merged and their energies summed. The energy of individual interactions was blurred by additive Gaussian noise with variance $\Sigma_i^2 = 1/2.35^2 \times ((6\,keV)^2 + (2.2\% \times \epsilon_i)^2)$, FWHM. The interactions were indexed arbitrarily, and the correct order of the sequence was stored for evaluation purposes. A lower-energy detection threshold of 10 keV was applied. The time stamp was blurred using 8 ns Gaussian noise. A 8 ns time window, consistent with NEC measurements for rat and mouse phantoms, was applied for coincidence gating. No dead time model was used in the simulation of the detectors.

The performance of four positioning schemes for PMIEs was investigated:

(i) Earliest Interaction (EI): The interaction with the smallest non-blurred time stamp was selected. This ideal scheme gives an upper bound on the performance of the positioning algorithm, although time resolution limitations restrict its use in practice.

(ii) Maximum A Posteriori (MAP): The full sequence was reconstructed using the example robust maximum-likelihood and robust maximum a posteriori methods described above. The event was positioned at the location of the estimated first interaction.

(iii) Energy Weighted Mean (EWM): The event was positioned at the energy-weighted mean position of the interactions. This scheme is standard for conventional PET block detectors.

(iv) Minimum Pair Distance (MPD): Both coincident events are first roughly positioned (for example, using EWM). The interaction closest to the rough location of the other coincident photon event is selected. This scheme is based on the preference of 511 keV photons to scatter forward. Unlike in MAP, the energy measurements are not used.

Discarding PMIEs was not considered, as one-interaction events are only a small fraction (e.g., 6.2%) of all coincidence photon events.

To identify the EI with MAP, the full sequence of interactions is reconstructed. For $N \geq 5$, the size of the combinatorial search space (N!) is greater than 60. Therefore, for $N \geq 5$, the MPD scheme was used instead of MAP for identifying the EI. Unlike MAP, the search space size in MPD grows linearly. In addition, for N large, the energy depositions are small, which means that in most interactions the photon scatters forward. Hence, MPD performs well for $N \geq 5$.

The simplest measure of the quality of the positioning is the recovery rate, defined as the fraction of all the processed single-photon events for which the first interaction is correctly identified. This figure of merit is not applicable for unconstrained positioning methods such as EWM. The recovery rate was evaluated in a variety of situations: for varying between zero and one, for stochastic and non-stochastic optimization, for PMIEs with number of interactions varying between one and six, and for varying energy resolution (0%, 3%, and 12% FWHM at 511 keV) and spatial resolution (1×1×1 and 1×5×1 mm³ detector voxels). To consider the influence of positioning methods on the final image quality, three components were investigated: the detector point-spread function (PSF), the contrast versus noise trade-off, and the reconstructed resolution.

A collimated single-photon, 1D point spread function (PSF) was measured for three incident angles (0, 30, and 60 degrees) and for all four positioning methods (EI, MAP, MPD, and EWM). A infinitely thin needle beam of 511 keV photons was simulated in GRAY and aimed at the center of a detector voxel in the middle of the panel, as shown in FIG. 6A. The events were positioned and their transverse coordinate (i.e., along $e_y$) histogrammed. The axial coordinate (i.e., along $e_z$) was also histogrammed for the normal (i.e., 0 degrees) beam. To assess the extent of backscatter, and investigate depth-dependent effects, 2D PSFs were also generated by histogramming the events' estimated positions along both $e_x$ and $e_y$.

Figure 6C:
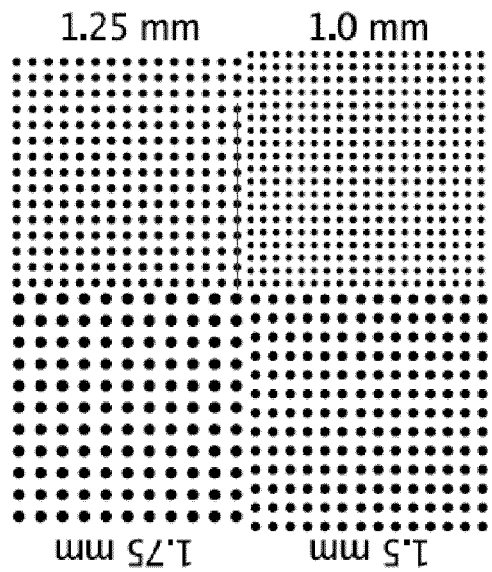
FIGS. 6A-C show a collection of phantoms used in an example quantitative evaluation, where
Figure 6B:
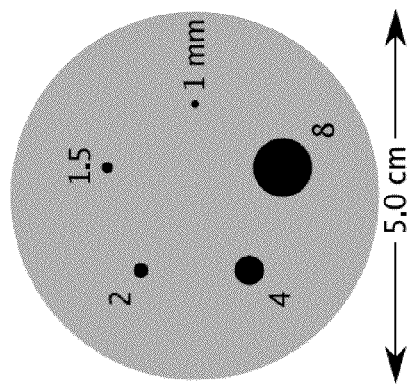
Figure 6A:
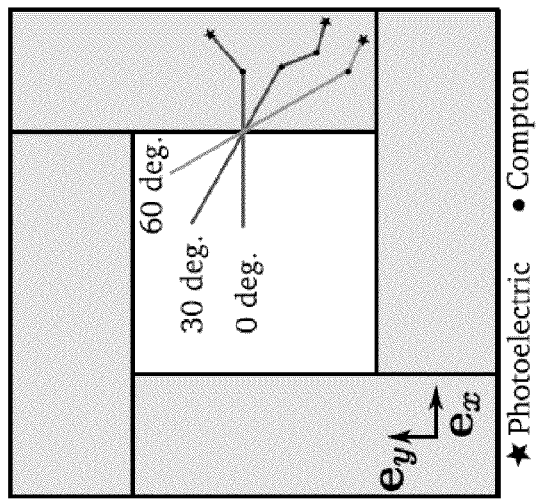

FIGS. 6A-C show a collection of phantoms used in the example quantitative evaluation. FIG. 6A shows three beams, with incident angles 0, 30, and 60 degrees, that were simulated. FIG. 6B shows a contrast phantom, including a 2.5 cm radius, 6 cm long cylinder filled with a warm solution of activity, in which were placed five hot spheres of size 1, 1.5, 2, 4, and 8 mm. The activity was ten times more concentrated in the hot spheres than in the background cylinder. FIG. 6C shows a hot sphere phantom, including four sphere patterns, all in the same central plane. The spheres extended to the edge of the 8×8×8 cm³ FOV, and their diameters were 1, 1.25, 1.5, and 1.75 mm. The spacing between the centers was twice the diameter.

The contrast phantom, as shown in FIG. 6B, was simulated to assess the quantitative contrast recovery. The phantom had a total of 800 μCi, and five seconds of acquisition were simulated, yielding 14.6 million coincident events. List-mode 3D-OSEM, with 10 million events per subset, was used for the reconstruction (Pratx et al., Fast, accurate and shift-varying line projections for iterative reconstruction using the GPU, IEEE Trans. Med. Imaging, 28, 2009, pp. 435-45). The contrast was measured in the reconstructed image as a function of iteration number. Mean reconstructed activity was measured in the hot spheres by using spherical 3D regions-of-interest (ROIs), as shown by example in FIG. 6B. Background activity was evaluated by averaging the reconstructed intensity in two cylindrical ROIs placed off of the central axial plane. Noise was approximated by the spatial standard deviation in the background ROIs, normalized by the mean background intensity. The peak value of the contrast-to-noise ratio (CNR) was computed over all the iterations.

A high-resolution sphere phantom, as shown in FIG. 6C, was simulated to consider the effects of the positioning on image resolution. The phantom included four quadrants of spheres in air, all in the central axial plane, placed all the way up to the edge of the 8×8×8 cm³ system FOV. The spheres were 1, 1.25, 1.5, and 1.75 mm in diameter. Their centers were placed twice their diameter apart. The phantom had a total of 800 μCi and five seconds of acquisition were simulated, yielding 27.2 million coincident events. The reconstructed sphere size (FWHM) was measured by fitting a Gaussian mixture with offset to 1D profiles through the reconstructed image. The 1 mm spheres were too small relative to the voxel size for their reconstructed FWHM to be reliably assessed.

Recovery Rate: The recovery rate is the fraction (e.g., %) of the processed single-photon events for which the first interaction is correctly identified. All recovery rates were evaluated based on at least 10 million events, and are subject to statistical measurement error below 0.02%. Some positioning methods, such as EWM, do not identify the first interaction, but rather estimate the position directly. The recovery rate is undefined for these methods.

Figure 7:
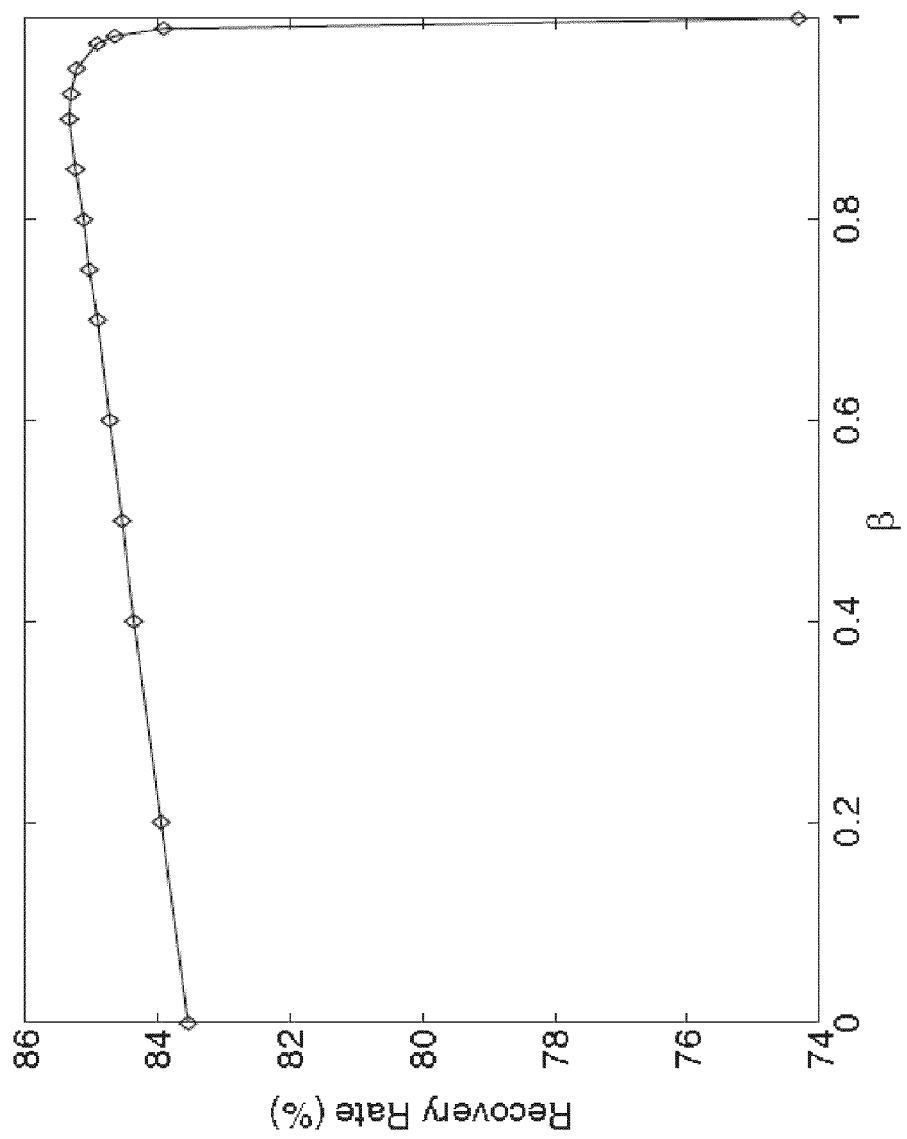
FIG. 7 shows a success rate in positioning a first interaction with an example MAP method as a function of parameter $\beta$.
Figure 8A:
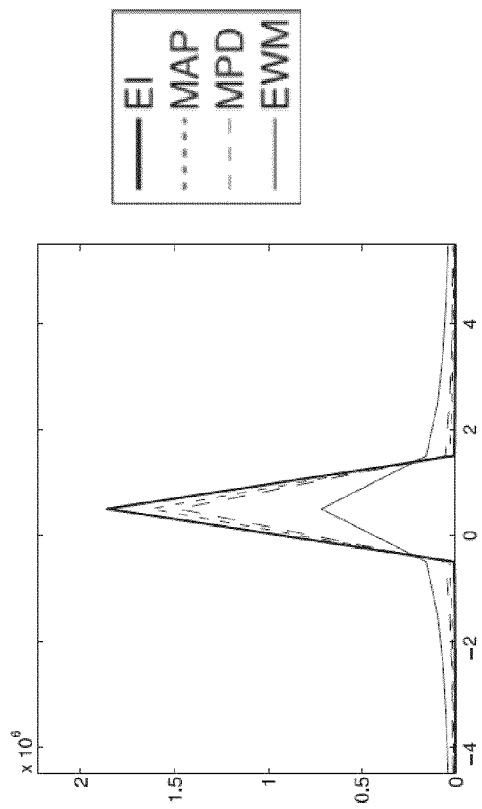
FIG. 8A shows 1D axial PSF for a normal beam (0 degree incident angle)
Figure 8C:
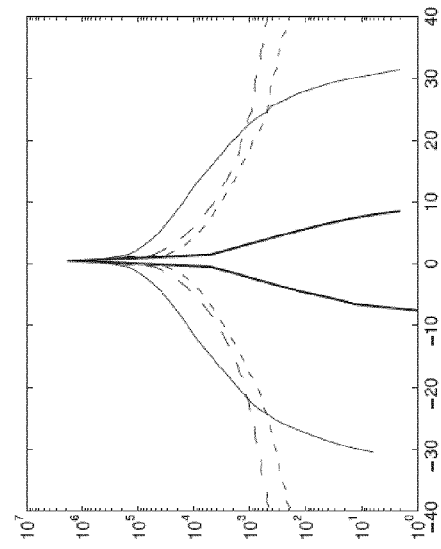
FIG. 8C shows 1D tangential PSF for a 30 degree beam.
Figure 8B:
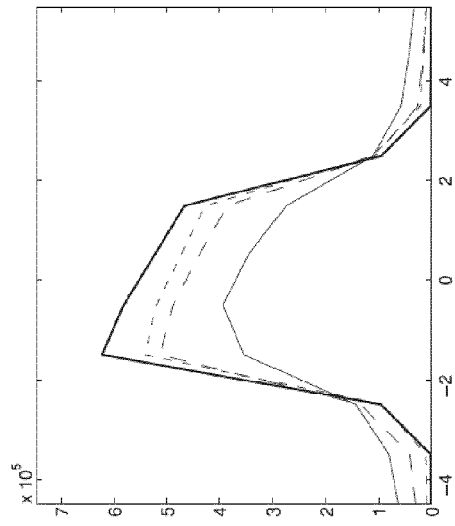
FIG. 8B shows 1D tangential PSF for the same normal beam.
Figure 8D:
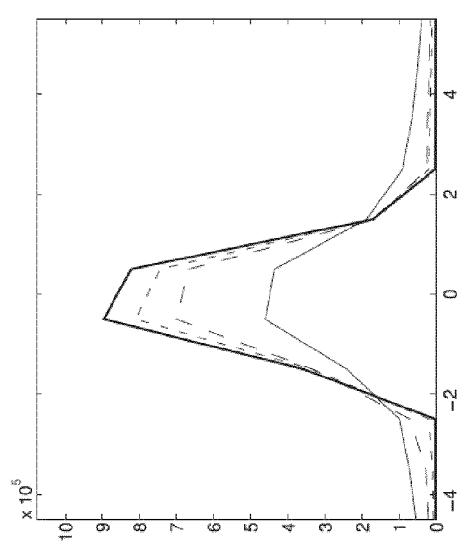
FIG. 8D shows 1D tangential PSF for a 60 degree beam.

For the example MAP positioning scheme, the recovery rate was computed for $\beta$ varying between zero and one, as shown in FIG. 7. The highest recovery rate (85.2%) was obtained for $\beta=0.85$, for the contrast phantom. This value is slightly higher than that obtained for $\beta=0$ (83.5%), which shows that use of prior information increases the quality of the estimation.

For MAP, the worst performance is reached for $\beta=1$, when only the prior probability is optimized. Yet, in this case, the recovery rate (74.3%) was still larger than for MPD (69.9%). Although both methods rely on the physics of y-ray transport and ignore the energy measurements, MAP with $\beta=1$ is a more accurate a priori probability computed from the trajectory total cross-section.

TABLE 1

| Positioning Methods | Beam 0° | Beam 30° | Beam 60° | Contrast Phantom |
|---|---|---|---|---|
| MAP (first interaction) | 84.3 | 86.2 | 83.6 | 85.2 |
| MPD (first interaction) | 76.6 | 71.9 | 70.2 | 69.4 |

TABLE 2

| Positioning Methods | PE Only | 1 CS + PE | 2 CS + PE | 3 CS + PE | 4 CS + PE | 5 CS + PE | Global |
|---|---|---|---|---|---|---|---|
| MAP (1st interaction) | 100 | 76.7 | 85.6 | 84.8 | — | — | 85.2* |
| MPD (1st interaction) | 100 | 52.1 | 64.1 | 75.8 | 82.4 | 86.4 | 69.4 |
| MAP (Full sequence) | 100 | 76.7 | 78.3 | 67.0 | — | — | 77.6† |

*For $N \geq 5$, the first interaction is estimated using MPD because the large size of the combinatorial search space ($\geq 60$) makes the identification of the correct sequence impractical.
†Computed only based on events with $N \leq 4$.

TABLE 3

| Positioning Methods | 1 × 1 × 1 mm³ | | | 1 × 5 × 1 mm³ | | |
|---|---|---|---|---|---|---|
| | 0.5%† | 2.5%† | 12%† | 0.5%† | 2.5%† | 12%† |
| MAP (1st interaction) | 90.0 | 89.6 | 88.1 | 85.5 | 85.2 | 61.5 |
| MPD (1st interaction) | | 69.4* | | | 69.4* | |

*The MPD scheme does not use energy information.
†FWHM at 511 keV.

TABLE 4

| Interaction Position | PE Only | 1 CS + PE | 2 CS + PE | 3 CS + PE | Global |
|---|---|---|---|---|---|
| Sub-voxel sampling | 100 | 76.7 | 85.0 | 84.8 | 85.2 |
| Voxel center | 100 | 68.2 | 75.9 | 72.5 | 78.8 |

The recovery rate varies with the photon angle of incidence, as shown in Table 1. The example MAP struggles most with large photon incident angles (such as 60 degrees), where the photon is more likely to interact with multiple panels. The MPD scheme performs best for photons impinging normally on the detector. For the contrast phantom setup, the number of mispositioned events with MAP is a factor of two lower compared to MPD: 30.6% versus 14.8%.

The recovery rate also depends on the number of times the annihilation photon interacts with the detector, as shown in Table 2 (CS indicates Compton scatter, PE indicates photoelectric). MAP's ability to find the earliest interaction is not substantially degraded by an increasing number of interactions. Although the size of the search space increases linearly, so does the number of measurements.

MAP has the ability to recover the full sequence of interactions, which is useful in certain applications. The recovery rate for the full sequence is provided in the third row of Table 2.

The specifications of the detector technology, including the energy resolution and intrinsic spatial resolution, affect the performance of the example MAP scheme. Table 3 shows the recovery rate (%) for MAP and MPD as a function of energy resolution and detector voxel size. Three levels of energy blur were considered: 0.5%, 2.5%, and 12% FWHM at 511 keV. Two levels of depth resolution were also investigated: 1 and 5 mm. For MAP, $\beta=0.85$ was used for all measurements. It should be noted that was only optimized for a system with 2.5% energy resolution and 5 mm depth resolution.

For the example MAP method, higher detector spatial and energy resolution help position correctly a larger fraction of PMIEs. Also, MAP's recovery rate is less sensitive to the energy resolution than to the detector voxel size.

An example robust objective uses stochastic optimization via sub-voxel sampling to account for the geometrical properties of the detector voxels. Table 4 shows that the stochastic approach results in a higher recovery rate compared to a deterministic one (where, for example, the interactions are assumed to occur at the center of the detector voxel).

Point-Spread Function: FIG. 8 shows the detector coincident PSFs for all four example positioning methods. For a normal beam (0 degrees), the PSF was plotted along the axial (FIG. 8A) and tangential (FIG. 8B) dimensions. The tangential component of the PSF was also plotted for 30 degrees (FIG. 8C) and 60 degrees (FIG. 8D) beams. Due to the 5 mm depth resolution of the example detector, the PSF is wider and asymmetric for photons incoming at an oblique angle. The PSF is not normalized, and therefore a higher peak value indicated that more counts are correctly positioned at the PSF center. The worst case error is smaller for EWM ($\approx$30 mm) than for MAP or MPD (40 mm), because the earliest interaction pulls the center of mass towards itself. Nevertheless, the average error is lower for both MAP and MPD than for EWM.

Figure 9:
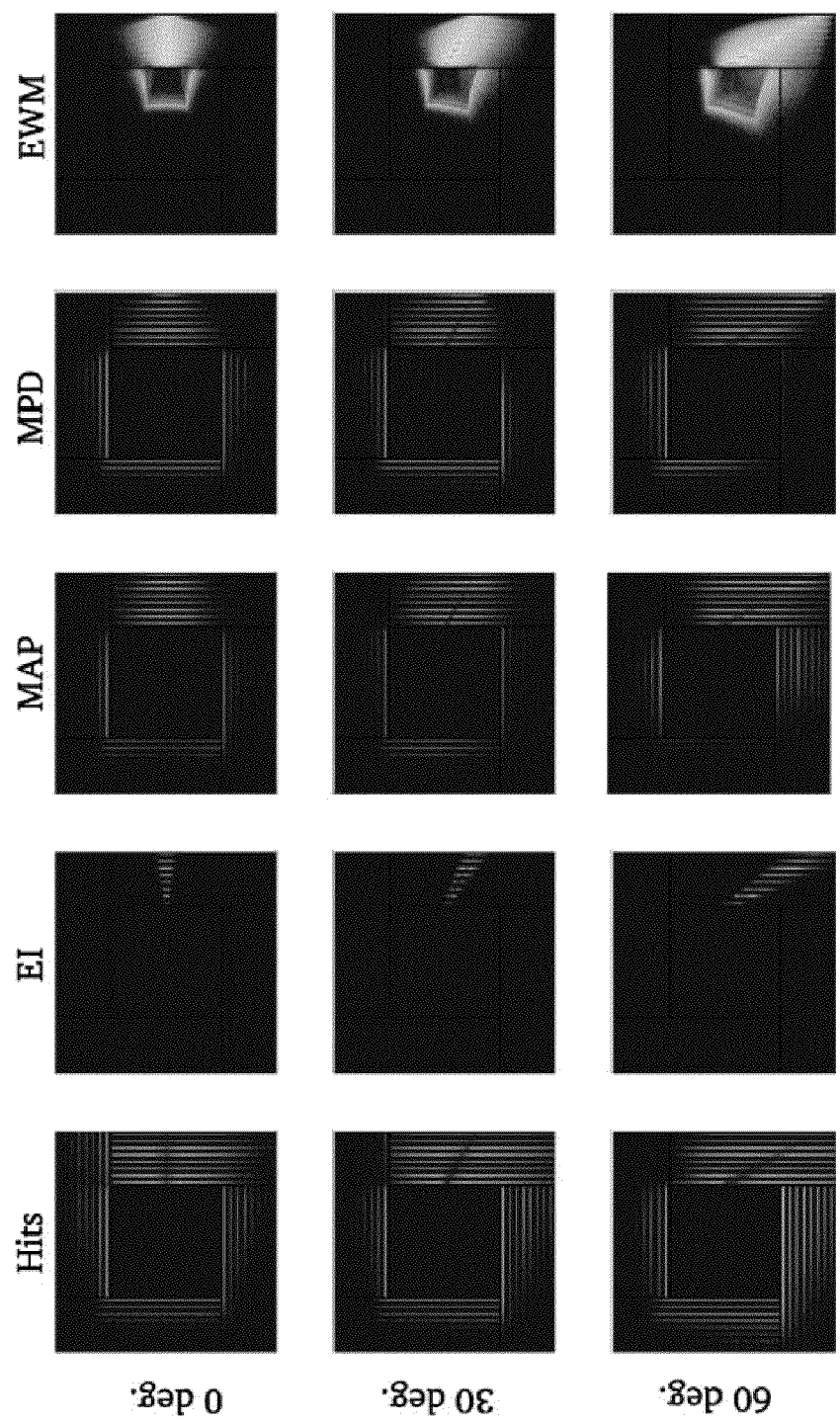
FIG. 9 shows a point-spread function (PSF) (2D) for three beam angles (top: 0 degree, middle, 30 degree, bottom, 60 degree)

FIG. 9 is a 2D representation of the PSF for the same beam angles (0, 30, and 60 degrees). All the PSFs are drawn using the same logarithmic scale, as the PMIEs mostly affect the tails of the PSF. The first column is a histogram of all the interactions, as recorded by the system (raw hits). The second to fifth columns show histograms of the position estimate for the EI, MAP, MPD, and EWM schemes, respectively. In addition, they provide some insight on how the interaction depth affects the positioning. For the EWM scheme, some PMIEs are positioned outside of the detector volume. This occurs when the photon back-scatters and deposits energy in two opposite detector panels, which places the center of mass of the interactions towards the center of the system. The characteristic profile of these interactions is produced by the fixed repartition of the 511 keV between the front and back interactions for a given back-scattering angle. As a result, the distribution of the EWM outlines the box-shaped geometry of the scanner.

Reconstructed Contrast: The system PSF affects the final image quality. Therefore, the contrast versus noise trade-off was investigated for five hot spheres in a warm background of activity (FIG. 6B). FIG. 10 shows the images reconstructed using 100 sub-iterations of list-mode OSEM for all four positioning methods: EI, MAP, MPD, and EWM. The four pictures are shown on the same intensity scale to facilitate the comparison. Only two spheres can be resolved for EWM. For the other positioning schemes, all but the smallest sphere are resolved.

FIG. 11 shows the contrast versus noise in the reconstructed images for the five spheres: 8 mm (FIG. 11A), 4 mm (FIG. 11B), 2 mm (FIG. 11C), 1.5 mm (FIG. 11D), and 1 mm (FIG. 11E). A total of 100 list-mode 3D-OSEM sub-iterations are displayed. The non-monotonic behavior of the noise is caused by the very coarse nature of the early image estimates.

Unlike the contrast recovery, the noise is not affected by mispositioning. Independently of the positioning method, the contrast is degraded by small angle tissue scatter and by random coincidences (randoms rate is around 10.6%). For this reason, it never reaches its true value (10:1), even for the ideal EI positioning scheme, which provides the highest contrast recovery (8.6 to 1). For the largest sphere, the contrast is 10% higher for MAP (7.5 to 1) than for the MPD scheme (6.8 to 1). The contrast difference is even greater for the smaller spheres: for the 2 mm sphere, the contrast is 24% higher for MAP than for MPD. It should be noted also that the contrast of the smallest spheres (1 and 1.5 mm) did not converge within a hundred iterations; however the noise prevents iterating further.

The EWM method demonstrated the worst performance for this task. The contrast is degraded to the extent that the small spheres ($\leq 2$ mm) cannot be resolved. The contrast of the largest sphere is 46% lower, compared to MAP.

The CNR (FIG. 11F) provides a rough estimate of the detectability of hot lesions in a background. Lesion with CNR greater than 4 (shown as a dotted line) are usually detectable, even though observer experience and object shape can also affect the detectability. The dotted line represents the threshold for Rose criterion. According to this criterion, the 1 mm sphere can only be detected when the ideal EI positioning scheme is used. The 1.5 mm and 2 mm spheres are not detectable when EWM is used. The CNR is systematically higher for MAP than for MPD.

Reconstructed Sphere Resolution: The hot spheres phantom (FIG. 6C) was used to evaluate how the spatial resolution is affected by positioning when iterative 3D-OSEM reconstruction is used. FIGS. 12A-D show the reconstructed images at 50 iterations for the four positioning methods (EI (FIG. 12A), MAP (FIG. 12B), MPD (FIG. 12C), and EWM (FIG. 12D)). The spheres are best resolved for the ideal EI scheme. MAP and MPD appear to perform similarly, but EWM shows substantial degradation of the spatial resolution.

Further investigation was performed by measuring the reconstructed FWHM of the spheres. This was done by fitting a Gaussian mixture with offset to multiple horizontal 1D profiles through the center of the spheres. The results of these measurements are reported in FIG. 13, for the 1.75 mm (FIG. 13A), 1.5 mm (FIG. 13B), and 1.25 mm (FIG. 13C) sphere sizes. Since the ML estimate is non-linear, the reconstructed FWHM should be analyzed with care and should not be interpreted in terms of modulation transfer function. However, it defines the ability of the algorithm to distinguish small lesions that are close to each other. It should also be noted that the reconstructed sphere FWHM is not expected to be equal to the real sphere size.

Due to parallax blurring and despite 5 mm depth resolution, the reconstructed sphere size is degraded for spheres away from the center of the FOV. The ideal EI scheme provides the best reconstructed FWHM, followed by MAP and MPD. Due to fewer mispositioned events, the reconstructed 1.75 mm spheres were on average 5.6% smaller for MAP than for MPD. As observed in FIG. 12D, EWM adds a substantial amount of blur to the reconstructed images. The profile through the 1.75 mm spheres (FIG. 13D) shows that, besides the FWHM, the contrast of the spheres is affected by positioning.

Example robust Bayesian methods have been provided for reconstructing sequences of interactions in detectors, allowing identification of the first interaction in the sequence. When MAP is used in an example embodiment, two times fewer events are mispositioned compared to MPD, a simpler algorithm. As a result, the PSF has lower tails and higher peak value, because more events are positioned to the correct LOR. MAP is also less susceptible to mispositioning events in which the photon undergoes back-scatter. This directly affects the reconstructed image quality. The contrast is higher for MAP positioning that for MPD. Mispositioning causes contrast loss because events that were emitted from the hot lesion are positioned in the background. The CNR is greater for MAP than for MPD and EWM, which implies that small lesions have a better chance of being detected in a clinical setting. In addition, MAP provides better quantitative accuracy. Images reconstructed using MAP positioning show higher spatial resolution, which allows the detection of hot objects.

The full sequence of interactions can also be reconstructed by optimizing the prior distribution alone (i.e., $\beta=1$ in MAP). Like MPD, this example approach has the advantage that energy measurements are not needed. Furthermore, MAP with $\beta=1$ can outperform MPD (e.g., by 4.4%, as shown in FIG. 7).

The size of the search space used for recovering the first interaction grows linearly with N, as does the number of energy measurements. Therefore, the performance of the example MAP method is maintained even as N increases. When recovering the full sequence, the size of the search space increases exponentially with N; hence, the recovery rate for complete sequences drops sharply for N=4.

Uncertainty in the locations of the interactions (within the detector voxel boundaries) translates into uncertainty in the scatter angle, which, in turn, yields uncertainty on the energy deposited. Position uncertainty in $1 \times 5 \times 1$ mm$^3$ detector voxels causes an equivalent energy blur far greater than 12% FWHM at 511 keV. When the interactions are constrained to fixed detectors voxels, the range of energies that can be deposited is often much larger than the energy resolution of the system.

Therefore, good spatial resolution is more important than good energy resolution for estimating correctly the order of the interactions.

PMIEs have been previously corrected using a simple positioning method (such as EWM), and then by incorporating an accurate model of the PSF to reconstruct the images. However, by effectively deconvolving the PMIE blur, this approach amplifies the noise. It is therefore preferable to use a positioning method, such as the example MAP method, prior to reconstruction, to estimate the location of the first interaction. Incorporating the resulting PSF into the reconstruction will generate less noise amplification because such a PSF is narrower. This requires, however, that crystals can be individually read out.

The described validation of the example MAP scheme was carried out based on simulations that included the standard Compton model based on the Klein-Nishina formula, the accurate linear attenuation coefficients from published databases, and the standard photoelectric model. Other physical effects can occur, such as characteristic X-ray production, Raleigh scattering, Bremsstrahlung and Doppler broadening, etc. Furthermore, the electron is neither free nor at rest, and therefore the Klein-Nishina formula is not accurate for Compton scattering of low (<100 keV) energy photons. The example method was therefore applied to a dataset using GATE, a more detailed Monte-Carlo package that incorporates all these effects (except Doppler broadening). For a point source in the center, the recovery rate dropped from 85.0% to 82.4% for MAP, and from 70.1% to 67.9% for MPD. This drop is mostly caused by the production of a characteristic X-ray that can propagate beyond boundaries of the detector voxel, in which case the number of interactions recorded increases. Doppler broadening was not modeled in any of the simulations. For 511 keV photons, Doppler broadening blur is at most 6 keV FWHM. Energy blurring remains dominated by the finite resolution of the detectors. In addition, high recovery rate (e.g., 84.5%) can still be achieved even with larger energy blur.

A particular example method assumes that the photon incoming energy $e_0$ and the location of other coincident photon p are available. While true for PET, these assumptions should not be made for other modalities that may be assisted under other embodiments of the present invention, such as but not limited to single photon emission computed tomography (SPECT) or Compton cameras. Example methods, however, can be generalized for these modalities. The incoming energy $e_0$ can be estimated by summing the energies of all the interactions. When p is unavailable, the likelihood should not include the first interaction because the scatter angle $\cos \hat{\theta}_1$ cannot be computed.

The example MAP objective can be readily extended to be used as criteria for rejecting tissue scattered events and random coincidences. An example formulation assumes that the incoming photon energy $e_0$ is 511 keV, and that the incident angle is given by the location p of the other photon pair. When the photon scatters in tissue or is paired up incorrectly (random coincidence), the assumption does not hold. As a result, no sequence might be attributed a high probability, and the event can be discarded.

MAP positioning according to example embodiments of the present invention can also be applied to crystals other than CZT. In a nonlimiting example, high-resolution detectors with depth-of-interaction capabilities can be built from lutetium oxyorthosilicate (LSO) coupled to thin position-sensitive avalanche photodiodes (PSAPD). These detectors do not offer as good an energy resolution as CZT, but the example MAP positioning scheme has high recovery rates even with 12% energy resolution FWHM. It should also be noted that, due to a higher photo-fraction, PMIEs occurs less often in LSO than in CZT.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. A method for determining a sequence of energy interactions in a detector, the method comprising:
   receiving a plurality of discrete energy interactions in a plurality of detector voxels;
   forming a plurality of possible sequences of interaction based on said received plurality of discrete energy interactions;
   for each of said plurality of possible sequences of interaction, computing an a posteriori probability, the a posteriori probability being based on a likelihood that the possible sequence of interaction is consistent with said received plurality of discrete energy interactions; and
   selecting one of said formed plurality of possible sequences of interaction based on said computed a posteriori probability;
   wherein said receiving a plurality of discrete energy interactions comprises receiving from the detector a plurality of signals corresponding to particular detector voxel locations and a plurality of energy measurements;
   wherein said computing an a posteriori probability comprises;
   for each of the plurality of detector voxels in the particular sequence, generating a distribution of multiple positions within the detector voxel;
   determining a plurality of realizations by selecting at least one of the generated multiple positions for each detector voxel in the particular sequence;
   for each of said determined realizations, computing an a posteriori probability; and
   combining said computed a posteriori probability over all of said determined plurality of realizations to provide said computed a posteriori probability objective for the particular sequence.

2. The method of claim 1, wherein said forming a plurality of possible sequences comprises determining all possible permutations of an order of the plurality of discrete energy interactions.

3. The method of claim 1, wherein said computing an a posteriori probability comprises:
   calculating a hypothetical energy for each of the interactions within said plurality of possible sequences of interaction;
   comparing said calculated hypothetical energy to said received plurality of energy measurements.

4. The method of claim 3, wherein said calculated hypothetical energy is computed using Compton kinematics.

5. The method of claim 3, wherein said computing an a posteriori probability further comprises:
   providing a probability for each of said plurality of possible sequences based on prior knowledge.

6. The method of claim 5, wherein said providing a probability further comprises:
obtaining a probability distribution of possible trajectories of a photon within the detector voxels based on physics of gamma ray transport prior to receiving the energy measurements.

7. The method of claim 6, wherein said obtaining a prior probability comprises:
computing a total cross-section for all possible trajectories based on physics of gamma ray transport;
determining an a priori distribution of said plurality of possible sequences based on said computed total cross-section.

8. The method of claim 1, wherein said computing an a posteriori probability comprises:
calculating a hypothetical energy for each of the interactions within said plurality of possible sequences of interaction;
comparing said calculated hypothetical energy to said received plurality of energy measurements to determine a first probability;
providing a probability for each of said plurality of possible sequences based on prior knowledge to determine a second probability;
combining said determined first probability and said second probability to compute said a posteriori probability.

9. The method of claim 1, wherein the detector comprises a detector for positron emission tomography (PET).

10. The method of claim 1, wherein said determining a plurality of realizations of positions comprises performing a 3D sampling of distributions within the detector voxels.

11. The method of claim 10, wherein said performing a 3D sampling comprises performing Monte Carlo integration.

12. A signal processor configured to perform the method of claim 1.

13. A computing device configured to perform the method of claim 1.

14. A non-transitory medium containing computer-readable instructions that when executed cause a computing device to perform the method of claim 1.

15. An imaging system configured to perform the method of claim 1.

16. The imaging system of claim 15, further comprising:
at least one detector positioned to receive incoming photons from the source of incoming photons and generate a signal; and
a signal processor coupled to the at least one detector for receiving the generated signal;
said signal processor being configured to perform the method of claim 1.

17. A method for determining a sequence of energy interactions in a detector, the method comprising:
receiving a plurality of discrete energy interactions in a plurality of detector voxels;
forming a plurality of possible sequences of interaction based on said received plurality of discrete energy interactions;
for each of said plurality of possible sequences of interaction, computing an a posteriori probability, the a posteriori probability being based on a likelihood that the possible sequence of interaction is consistent with said received plurality of discrete energy interactions; and
selecting one of said formed plurality of possible sequences of interaction based on said computed a posteriori probability;
wherein said receiving a plurality of discrete energy interactions comprises receiving from the detector a plurality of signals corresponding to particular detector voxel locations and a plurality of energy measurements;
wherein said computing an a posteriori probability comprises:
calculating a hypothetical energy for each of the interactions within said plurality of possible sequences of interaction;
comparing said calculated hypothetical energy to said received plurality of energy measurements to determine a first probability;
providing a probability for each of said plurality of possible sequences based on prior knowledge to determine a second probability;
combining said determined first probability and said second probability to compute said a posteriori probability;
wherein said combining comprises:
providing a relative weight for said determined first probability and said second probability;
combining said first probability and said second probability using said provided relative weight.

18. A method for determining an interaction path of an incoming photon received from a source of emitted photons, the method comprising:
receiving a plurality of discrete interactions of a single gamma ray photon in a plurality of detector voxels;
determining all possible sequences for the plurality of discrete interactions based on said received plurality of discrete interactions;
for each of said all possible sequences, computing an a posteriori probability objective based on a weighted likelihood of the particular sequence based on energy measurements for said received plurality of discrete interactions and a weighted a priori probability; and
selecting the sequence having the maximum computed a posteriori objective over said all possible sequences;
wherein said computing an a posteriori probability objective comprises, for each of the all possible sequences:
for each of the plurality of detector voxels in the particular sequence, generating a distribution of multiple positions within the detector voxel;
determining a plurality of realizations by selecting at least one of the generated multiple positions for each detector voxel in the particular sequence;
for each of said determined realizations, computing an a posteriori probability; and
combining said computed a posteriori probability over all of said determined plurality of realizations to provide said computed a posteriori probability objective for the particular sequence.

19. The method of claim 18, further comprising:
selecting a first interaction based on said selected sequence.

20. The method of claim 19, further comprising:
determining a line of response (LOR) of the incoming photon based on said selecting a first interaction.

21. The method of claim 19, further comprising:
determining a direction for the incoming photon based on said selected sequence.

22. The method of claim 18, further comprising:
selecting a first and second interaction using said selected sequence; and
determining whether to accept or reject an event based on said selecting.

23. The method of claim 18, further comprising:
imaging a subject using said selected sequence.

24. A system for determining an interaction path of an incoming photon received from a source of emitted photons, the system comprising:
- detector means for receiving a plurality of discrete interactions of a single gamma ray photon in a plurality of detector voxels;
- means for computing an a posteriori probability objective for all possible sequences for the plurality of discrete interactions using a weighted likelihood of multiple distributed paths of the particular sequence based on energy measurements for the received plurality of discrete interactions and a weighted a priori probability of multiple distributed paths of the particular sequence; and
- means for selecting the sequence having the maximum computed a posteriori probability objective over all possible sequences;
- wherein said means for computing an a posteriori probability comprises:
- means for calculating a hypothetical energy for each of the interactions within said plurality of possible sequences of interaction;
- means for comparing said calculated hypothetical energy to said received plurality of energy measurements to determine a first probability;
- means for providing a probability for each of said plurality of possible sequences based on prior knowledge to determine a second probability;
- means for combining said determined first probability and said second probability to compute said a posteriori probability;
- wherein said means for computing an a posteriori probability comprises;
- means for generating, for each of the plurality of detector voxels in the particular sequence, a distribution of multiple positions within the detector voxel;
- means for determining a plurality of realizations by selecting at least one of the generated multiple positions for each detector voxel in the particular sequence;
- means for computing, for each of said determined realizations, an a posteriori probability; and
- means for combining said computed a posteriori probability over all of said determined plurality of realizations to provide said computed a posteriori probability objective for the particular sequence.

25. A method for determining a sequence of energy interactions in a detector, the method comprising:
- receiving a plurality of discrete energy interactions in a plurality of detector voxels;
- forming a plurality of possible sequences of interaction based on said received plurality of discrete energy interactions;
- for each of said plurality of possible sequences of interaction, computing an a posteriori probability comprising an a priori probability based on physics of energy transport;
- selecting one of said formed plurality of possible sequences of interaction based on said computed a posteriori probability;
- wherein said computing an a posteriori probability comprises;
- for each of the plurality of detector voxels in the particular sequence, generating a distribution of multiple positions within the detector voxel;
- determining a plurality of realizations by selecting at least one of the generated multiple positions for each detector voxel in the particular sequence;
- for each of said determined realizations, computing an a posteriori probability; and
- combining said computed a posteriori probability over all of said determined plurality of realizations to provide said computed a posteriori probability objective for the particular sequence.

* * * * *

UNITED STATES PATENT AND TRADEMARK OFFICE
CERTIFICATE OF CORRECTION

| | | |
|---|---|---|
| PATENT NO. | : 8,274,054 B2 | Page 1 of 1 |
| APPLICATION NO. | : 12/607853 | |
| DATED | : September 25, 2012 | |
| INVENTOR(S) | : Pratx et al. | |

It is certified that error appears in the above-identified patent and that said Letters Patent is hereby corrected as shown below:

In the Specification:

Col. 14, lines 47-48    Please delete "Please amend the paragraph beginning at line 10, page 24 as follows:"

Col. 18, line 25    After "noted that" please insert -- β --

Signed and Sealed this
Sixth Day of August, 2013

Teresa Stanek Rea
*Acting Director of the United States Patent and Trademark Office*